(12) United States Patent
Zadno-Azizi et al.

(10) Patent No.: US 6,605,074 B2
(45) Date of Patent: *Aug. 12, 2003

(54) METHOD FOR CONTAINING AND REMOVING OCCLUSIONS IN THE CAROTID ARTERIES

(75) Inventors: Gholam-Reza Zadno-Azizi, Newark, CA (US); Mukund R. Patel, San Jose, CA (US); Ketan P. Muni, San Jose, CA (US); Celso J. Bagaoisan, Union City, CA (US); Hung V. Ha, San Jose, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/246,077

(22) Filed: Sep. 16, 2002

(65) Prior Publication Data

US 2003/0023227 A1 Jan. 30, 2003

Related U.S. Application Data

(63) Continuation of application No. 09/270,150, filed on Mar. 16, 1999, now abandoned.

(51) Int. Cl.$^7$ ............................................. A61M 31/00
(52) U.S. Cl. ...................................... 604/509; 604/507
(58) Field of Search .................................. 604/915–921, 604/507, 508, 509, 96.01, 104, 105, 106, 107, 101.01, 101.02, 101.03, 101.05; 606/191, 192, 193, 194; 600/585, 434

(56) References Cited

U.S. PATENT DOCUMENTS

| | | | |
|---|---|---|---|
| 3,144,868 A | 8/1964 | Jascalevich | 128/350 |
| 4,276,874 A | 7/1981 | Wolvek et al. | 128/1 D |
| 4,445,892 A | 5/1984 | Hussein et al. | 604/101 |

(List continued on next page.)

FOREIGN PATENT DOCUMENTS

| | | |
|---|---|---|
| DE | 38 04 849 A1 | 9/1988 |
| WO | WO 89/01309 | 2/1989 |
| WO | WO 95/01751 | 1/1995 |

(List continued on next page.)

OTHER PUBLICATIONS

"Coronary and Perifpheral Angioplasty: Historic Perspective" Myler, et al., II–Coronary and Peripheral Angioplasty. Chapter 9, pp. 171–185.

"Restenosis: The Clinical Issues" Hillegass, et al., II–Coronary and Peripheral Angioplasty, Chapter 22, pp. 415–435.

* cited by examiner

*Primary Examiner*—Manuel Mendez

(57) ABSTRACT

A method for the treatment of a stenosis or an occlusion in a blood vessel is disclosed in which a main catheter is first delivered to a site proximal to the occlusion. The main catheter may include an occlusive device at its distal end. An inner catheter or elongate member (e.g., a guidewire) having an occlusive device at its distal end is delivered to the site of the occlusion, and the occlusive device is activated at a site distal to the occlusion. A therapy catheter is then introduced to treat the occlusion. Next, a catheter is delivered just proximal to the occlusive device, and this catheter is used to aspirate and/or irrigate the area removing particles and debris. The aspiration and irrigation steps are preferably repeated until the particles and debris are removed. Perfusion may be performed by using a perfusion-filter distal of the lesion to be treated or a hypotube which extends beyond the occlusive device attached to the guidewire. The present invention provides for a minimally invasive procedure which can be performed quickly and efficiently, with reduced risks to the patient.

41 Claims, 23 Drawing Sheets

U.S. PATENT DOCUMENTS

| | | | |
|---|---|---|---|
| 4,456,011 A | 6/1984 | Warnecke | 604/28 |
| 4,468,216 A | 8/1984 | Muto | 604/43 |
| 4,511,354 A | 4/1985 | Sterling | 604/98 |
| 4,573,966 A | 3/1986 | Weikl et al. | 604/53 |
| 4,610,662 A | 9/1986 | Weikl et al. | 604/53 |
| 4,636,195 A | 1/1987 | Wolinsky | 604/53 |
| 4,655,746 A | 4/1987 | Daniels et al. | 604/53 |
| 4,692,139 A | 9/1987 | Stiles | |
| 4,696,668 A | 9/1987 | Wilcox | 604/101 |
| 4,705,507 A | 11/1987 | Boyles | 604/101 |
| 4,714,460 A | 12/1987 | Calderon | 604/28 |
| 4,748,982 A | 6/1988 | Horzewski et al. | 128/344 |
| 4,781,677 A | 11/1988 | Wilcox | |
| 4,790,812 A | 12/1988 | Hawkins, Jr. et al. | 604/22 |
| 4,790,813 A | 12/1988 | Kensey | 604/22 |
| 4,824,436 A | 4/1989 | Wolinsky | 604/53 |
| 4,832,028 A | 5/1989 | Patel | 128/344 |
| 4,838,268 A | 6/1989 | Keith et al. | 128/344 |
| 4,911,163 A | 3/1990 | Fina | 606/127 |
| 4,921,478 A | 5/1990 | Solano et al. | 604/53 |
| 4,926,858 A | 5/1990 | Gifford, III et al. | |
| 4,946,466 A | 8/1990 | Pinchuk et al. | 604/194 |
| 4,950,238 A | 8/1990 | Sullivan | 604/22 |
| 4,964,409 A | 10/1990 | Tremulis | 128/657 |
| 4,998,917 A | 3/1991 | Gaiser et al. | 604/96 |
| 5,000,743 A | 3/1991 | Patel | 606/194 |
| 5,035,686 A | 7/1991 | Crittenden et al. | 604/96 |
| 5,059,178 A | 10/1991 | Ya | 604/101 |
| 5,135,484 A | 8/1992 | Wright | 604/28 |
| 5,152,277 A | 10/1992 | Honda et al. | 128/4 |
| 5,163,906 A | 11/1992 | Ahmadi | 604/101 |
| 5,167,239 A | 12/1992 | Cohen et al. | 128/772 |
| 5,195,955 A | 3/1993 | Don Michael | 604/22 |
| 5,221,270 A | 6/1993 | Parker | 604/282 |
| 5,226,889 A | 7/1993 | Sheiban | 604/101 |
| 5,250,060 A | 10/1993 | Carbo et al. | 606/159 |
| 5,256,141 A | 10/1993 | Gencheff et al. | 604/53 |
| 5,279,546 A | 1/1994 | Mische et al. | 604/22 |
| 5,281,200 A | 1/1994 | Corso, Jr. et al. | 604/96 |
| 5,320,604 A | 6/1994 | Walker et al. | 604/96 |
| 5,320,605 A | 6/1994 | Sahota | 604/101 |
| 5,322,508 A | 6/1994 | Viera | 604/52 |
| 5,328,471 A | 7/1994 | Slepian | 604/101 |
| 5,342,306 A | 8/1994 | Don Michael | 604/101 |
| 5,380,284 A | 1/1995 | Don Michael | 601/101 |
| 5,395,311 A | 3/1995 | Andrews | 604/22 |
| 5,397,307 A | 3/1995 | Goodin | 604/96 |
| 5,403,274 A | 4/1995 | Cannon | 604/9 |
| 5,405,322 A | 4/1995 | Lennox et al. | 604/53 |
| 5,413,558 A | 5/1995 | Paradis | 604/101 |
| 5,415,635 A | 5/1995 | Bagaoisan et al. | 604/96 |
| 5,415,636 A | 5/1995 | Forman | 604/101 |
| 5,423,742 A | 6/1995 | Theron | 604/28 |
| 5,423,744 A | 6/1995 | Gencheff et al. | 604/53 |
| 5,439,000 A | 8/1995 | Gunderson et al. | 128/664 |
| 5,439,446 A | 8/1995 | Barry | 604/96 |
| 5,449,343 A | 9/1995 | Samson et al. | 604/96 |
| 5,458,573 A | 10/1995 | Summers | 604/101 |
| 5,458,574 A | 10/1995 | Machold et al. | 604/101 |
| 5,460,610 A | 10/1995 | Don Michael | 604/101 |
| 5,462,529 A | 10/1995 | Simpson et al. | 604/101 |
| 5,464,394 A | 11/1995 | Miller et al. | |
| 5,476,450 A | 12/1995 | Ruggio | 604/93 |
| 5,478,309 A | 12/1995 | Sweezer et al. | 604/4 |
| 5,484,412 A | 1/1996 | Pierpont | 604/101 |
| 5,496,346 A | 3/1996 | Horzewski et al. | 606/194 |
| 5,500,180 A | 3/1996 | Anderson et al. | 264/532 |
| 5,505,700 A | 4/1996 | Leone et al. | |
| 5,505,702 A | 4/1996 | Arney | 604/101 |
| 5,514,092 A | 5/1996 | Forman et al. | 604/101 |
| 5,599,307 A | 2/1997 | Bacher et al. | |
| 5,634,897 A | 6/1997 | Dance et al. | |
| 5,645,533 A | 7/1997 | Blaeser et al. | 604/164 |
| 5,674,198 A | 10/1997 | Leone | |
| 5,681,336 A | 10/1997 | Clement et al. | |
| 5,688,234 A | 11/1997 | Frisbie | |
| 5,779,721 A | 7/1998 | Nash | |
| 5,823,996 A | 10/1998 | Sparks | |
| 5,833,644 A | 11/1998 | Zadno-Azizi et al. | |
| 5,833,650 A | 11/1998 | Imran | |
| 5,879,361 A | 3/1999 | Nash | |
| 5,941,896 A | 8/1999 | Kerr | |
| 5,954,745 A | 9/1999 | Gertler et al. | |
| 6,022,336 A | 2/2000 | Zadno-Azizi et al. | |
| 6,135,991 A | 10/2000 | Muni et al. | |
| 6,295,989 B1 | 10/2001 | Connors, III | |

FOREIGN PATENT DOCUMENTS

| | | |
|---|---|---|
| WO | WO 95/09024 | 4/1995 |
| WO | WO 96/01079 | 1/1996 |
| WO | WO 96/15824 | 5/1996 |
| WO | WO 97/44082 | 11/1997 |
| WO | WO 98/26833 | 6/1998 |
| WO | WO 98/38929 | 9/1998 |
| WO | WO 98/38930 | 9/1998 |
| WO | WO 98/44982 | 10/1998 |
| WO | WO 99/22673 | 5/1999 |

OTHER PUBLICATIONS

"The Pathology of Interventional Coronary Artery Techniques and Devices" Waller, et al., II–Coronary and Peripheral Angioplasty, Chapter 24, pp. 449–476.

"Perfusion Angiplasty." Kereiakes, et al., II–Coronary and Peripheral Angioplasty, Chapter 25, pp. 477–494.

"Angiplasty and Interventional Vascular Procedures in the Peripheral, Renal, Visceral and Extracranial Circulation" Wholey, et al., II–Coronary and Peripheral Angioplasty, Chapter 33, pp. 600–628.

"DCA Device" (section) and summary III–Coronary Atherectomy, Chapter 35, pp. 642, 657, and 658.

"Percutaneous Coronary Rotational Angioplasty with the Rotablator" Bertrand, et al., III–Coronary Atherectomy, Chapter 36, pp. 659, 666 and 667.

"Extraction Atherectomy" III–Coronary Atherectomy, Chapter 37, pp. 669, 675–677.

"Zeppelin–1066: Flow Control and Protection During Carotid Angioplasty" Mirco Interventional Systems, Inc., Advertisement.

"Zeppelin–1066: Flow Control Improves Safety During CCF Emboliztion" Micro Interventional Systems, Inc., Advertisement.

"Zeppelin–1066: Provides Flow Control and Protection During Detachable Balloon Occulusion" Micro Interventional Systems, Inc., Advertisement.

"Zeppelin: Balloon Guiding Catheter" Micro Interventional Systems, Inc., *Advertisement*.

"Carotid Endarterectomy" Hershey/Calman, Atlas of Vascular Surgery, pp. 311–318, 1973.

"Percutaneouds Transluminal Angioplasty in Arteriosclerotic Internal Carotid Artery Stenosis" Bockenheimer, et al., AJNR,4:791–792, May/Jun. 1983.

"Percutaneous Transluminal Angioplasty of the Carotid Artery" Tsai, et al., AJNR, 7:349–358, Mar./Apr. 1986.

"Practical Aspects of Percutaneous Transluminal Angioplasty of the Carotid Artery" Tsai, et al., ACTA Radiologica, Supplementum 369, XIII Symposium Neuroradiologicum Stockholm, Jun. 1986.

"Transluminal Angioplasty for the Treatment of Carotid Arter Stenosis" Freitag, et al., VASA, Band 16, Heft 1, 1987.

"Feasibility of Percutaneous Transluminal Angioplasty for Carotid Artery Stenosis" Brown, et al., Journal of Neurology, Neuosurgery, and Psychiatry, 53(3): 238–243, Mar. 1990.

"New Triple Coaxial Catheter System for Carotid Angioplasty with Cerebral Protection" Theron, et al., AJNR, 11:869–874, Sep./Oct. 1990.

"Percutaneous Angioplasty of Artherosclerotic Carotid Arteries" Porta, et al., Cerebrovasc Dis., 1:265–272, 1991.

"Percutaneous Transluminal Angioplasty (PTA) of Supra–Aortic Arteries Especially the Internal Carotid Artery" Kachel, et al., Neuroradiology, 33(3): 191–194, 1991.

"Carotid Angioplasty: Haemodynamic and Embolic Consequences" Markus, et al., Cerebrovascular Diseases, Abstract 214, p. 259, Jul.–Aug. 1994.

"Carotid Endarterectomy: The Gold Standard" Zarins, Journal of Endovasculary Surgery, 3(1): pp. 10–15, Feb. 1996.

"Angiojet® System Used to Treat Stroke Victim" Possis Medical, Inc., News Release, Sep. 11, 1996.

"Current and Future Treatment of Carotid Bifurcation Atherosclerotic Disease: A Perspective" Becker, Journal of Vascular and Interventional Radiology, 8(1): 3–8, Jan.–Feb. 1997.

"Percutaneous Angioplasty of Atherosclerotic and Postsurgical Stenosis of Carotid Arteries" J. Teron et al., AJNR., 6:495–500, May/Jun. 1987.-

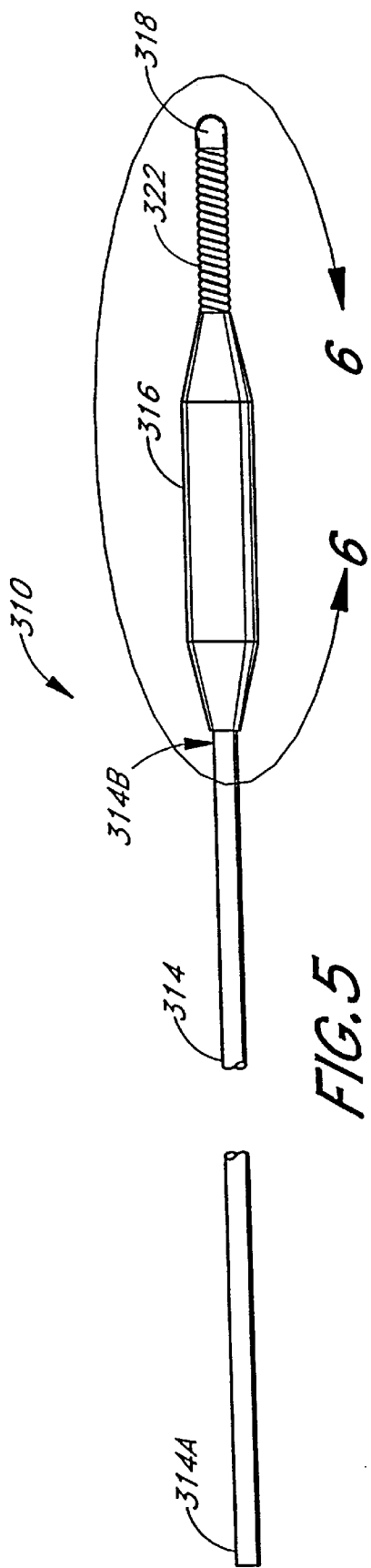
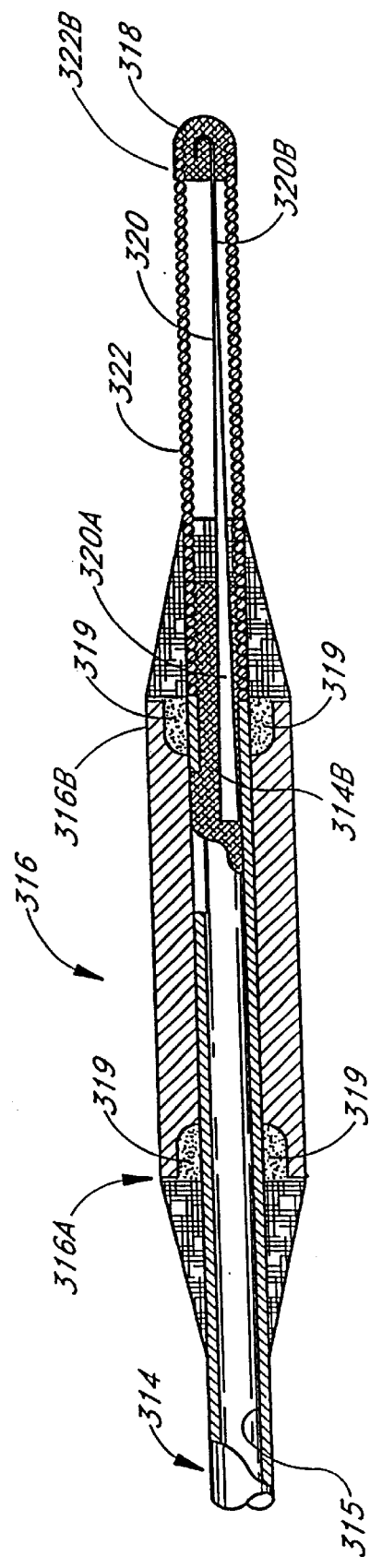

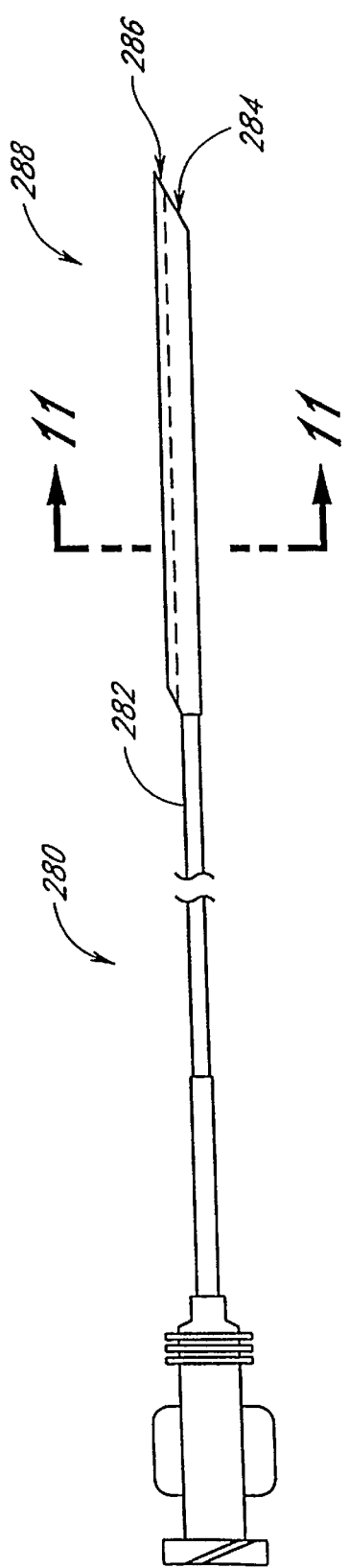
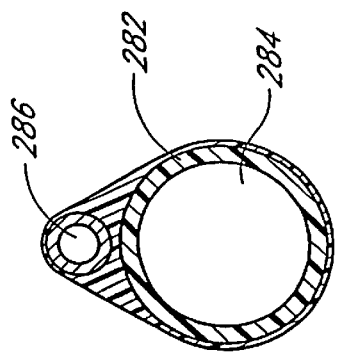
FIG. 10
FIG. 11

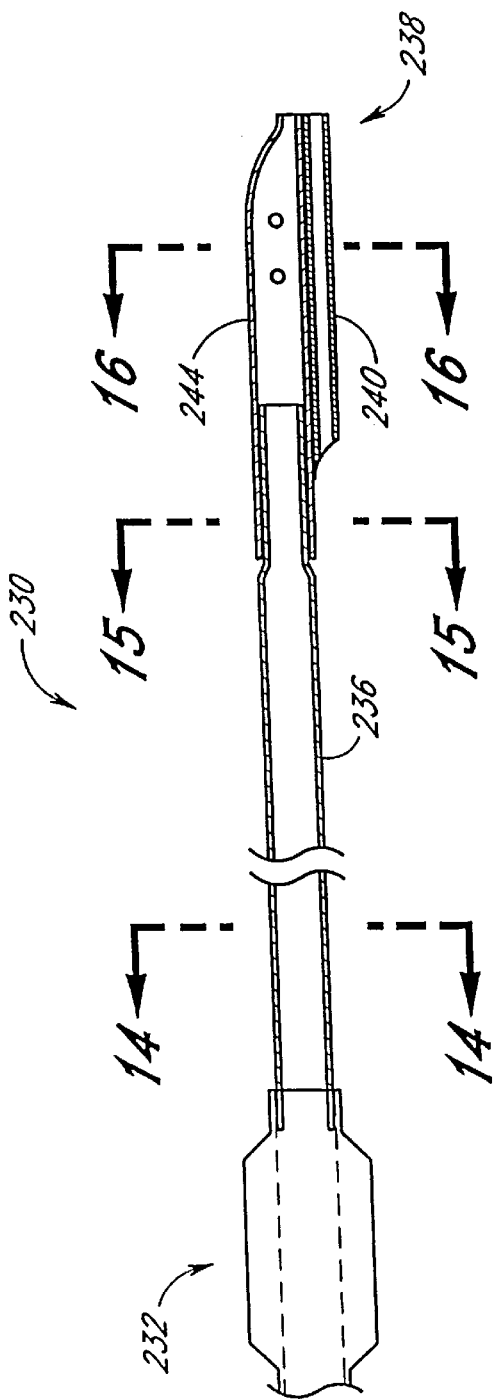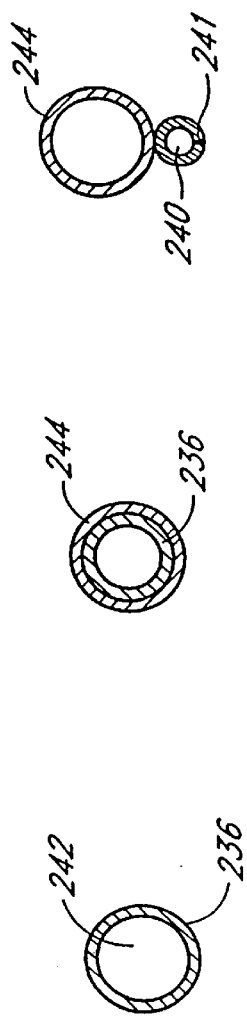

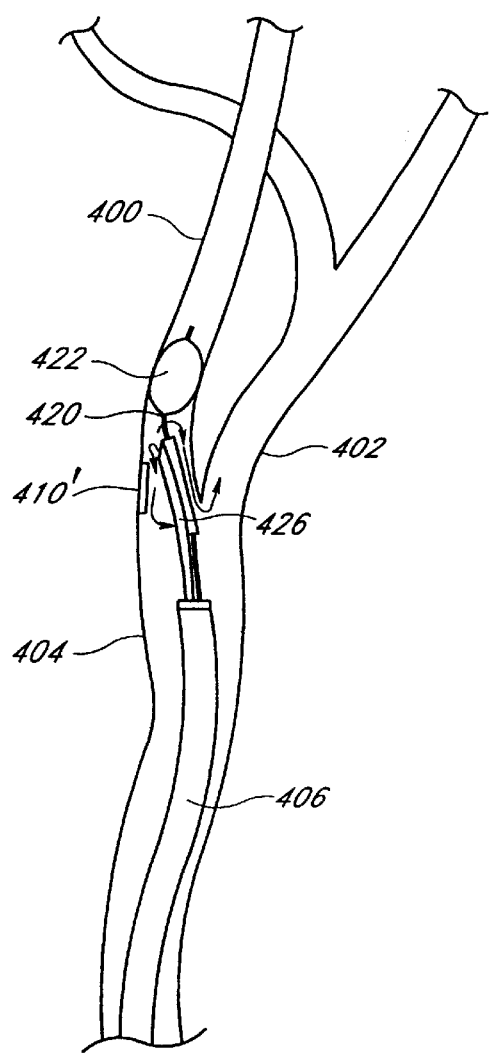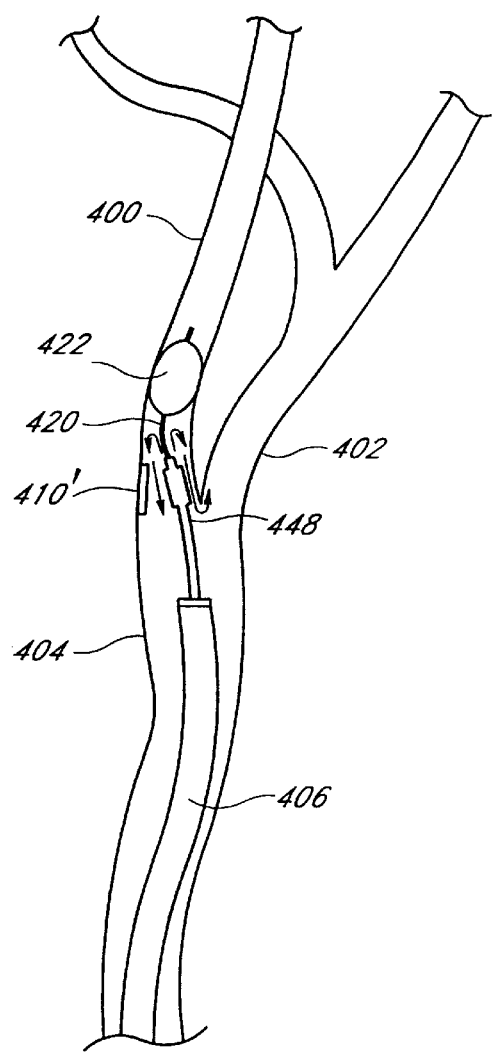
FIG.24
FIG.24A

METHOD FOR CONTAINING AND REMOVING OCCLUSIONS IN THE CAROTID ARTERIES

CROSS-REFERENCE TO RELATED APPLICATION

This application is a continuation of U.S. application Ser. No. 09/270,150, filed Mar. 16, 1999 now abandoned.

BACKGROUND OF THE INVENTION

1. Field of the Invention

The present invention relates to containment and removal of substances including emboli (such as from thrombi, plaque, and other types of material and debris) from blood vessels. The preferred embodiments are particularly advantages for use in the carotid arteries and other arteries above the aortic arch during diagnostic and therapeutic procedures.

2. Description of the Related Art

Human blood vessels often become occluded or completely blocked by plaque, thrombi, deposits, or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

The carotid arteries are the main vessels which supply blood to the brain and face. The common carotid artery leads upwards from the aortic arch, branching into the internal carotid artery which feeds the brain, and the external carotid artery which feeds the head and face. The carotid arteries are first narrowed and may eventually be almost completely blocked by plaque, and may further be complicated by the formation of thrombi (blood clots) on the roughened surfaces of the plaques. Narrowing or blockage of the carotid arteries is often untreatable and can result in devastating physical and cognitive debilitation, and even death.

Various types of intervention techniques have been developed which facilitate the reduction or removal of the blockage in the blood vessel, allowing increased blood flow through the vessel. One technique for treating stenosis or occlusion of a blood vessel is percutaneous balloon angioplasty. A balloon catheter is threaded through the patient's arterial system and inserted into the narrowed or blocked area, and the balloon is inflated to expand the constricted area. The fear of dislodging an embolus from an ulcerative plaque and the severe resulting consequences, however, has prevented the widespread use of angioplasty in the carotid arteries. Because of the potential complications, the options for minimally invasive treatment of the carotid arteries are severely limited.

Carotid endarterectomy is another type of intervention for removal of blockages from the carotid arteries. In endarterectomy, the carotid bifurcation is exposed through an incision in the neck of the patient. Clamps are placed on either side of the occlusion to isolate it, and an incision made to open the artery. The occlusion is removed, the isolated area irrigated and aspirated, and the artery sutured closed. The clamps are removed to reestablish blood flow through the artery. In carotid endarterectomy, the emboli and debris are contained and directed by activating and deactivating the clamps. For example, after the clamps are in place, one on the common carotid artery and one on the internal carotid artery, the particles are contained between the two clamps. After the occlusion is removed, the clamp on the common carotid artery is opened, allowing blood to flow into the previously isolated area toward the clamp on the internal carotid. This blood flow is then aspirated through an external aspiration tube. The common carotid artery is then reclamped, and the clamp on the internal carotid opened. This causes blood to flow into the previously isolated area toward the clamp on the common carotid artery. The flow is then aspirated. The clamp on the internal carotid artery is closed, and the artery is sutured closed. This method allows for the flushing of debris into the area where aspiration occurs.

Alternatively, this method of clamping and unclamping the carotid arteries can be done after the incision in the artery is sutured closed. Using this method, it is hoped that any particles in the internal carotid artery will be forced back to the common carotid artery, then into the external carotid area, where serious complications are unlikely to arise from emboli.

Carotid endarterectomy is not without the serious risk of embolization and stroke caused by particles of the blocking material and other debris moving downstream to the brain, however. There is therefore a need for improved methods of treatment for occluded carotid arteries which decrease the risks to the patient.

SUMMARY OF THE INVENTION

The present invention provides a novel method for containing and removing substances such as emboli from blood vessels. The method is particularly useful in bifurcated vessels, such as the carotid arteries and in other blood vessels above the aortic arch. In one embodiment of the method, there is provided at least one occlusive device such as a balloon or filter, a therapy catheter to treat the occlusion, and a source of aspiration to remove the debris created by the therapy. By utilizing the fluid pressure and flow within the blood vessel, this method can eliminate the need for a separate irrigation catheter and irrigation fluid. Alternatively, irrigation fluid may be provided to flush the area. The minimally invasive treatment allows occlusions to be treated more rapidly and less invasively than known methods, with reduced cost and risk to the patient.

In accordance with one aspect of the present invention, there is provided a method for the treatment of an occlusion in a carotid artery. A main catheter having a first occlusive device on its distal end is inserted into the artery, until the occlusive device is proximal to the occlusion. The first occlusive device is activated to occlude the artery proximal to the occlusion. An inner catheter having a second occlusive device on its distal end is inserted into the artery across the occlusion, until the occlusive device is distal to the occlusion. The second occlusive device is then activated to occlude the artery distal to the occlusion and create a working area surrounding the occlusion. By occlusive device is meant any device which is capable of preventing at least some particles or other debris from migrating downstream. Examples of occlusive devices include inflatable balloons, filters or braids, or other mechanical devices.

According to the foregoing aspect of the invention, a therapy catheter is then inserted into the working area and used to treat the occlusion. Appropriate treatment can include direct drug delivery to the site of the occlusion, angioplasty, cutting, scraping or pulverizing the occlusion, ablating the occlusion using ultrasound or a laser, deploying a stent within the artery, use of a thrombectomy or rheolitic device, or other treatments. Following treatment of the occlusion, the therapy catheter is removed. An aspiration catheter is then delivered to the working area, and the first occlusive device is deactivated to allow blood flow into the working area. Blood flow from collateral vessels prevent the movement of particles and debris downstream where they could cause serious complications. The blood flow also acts as irrigation fluid to create turbulence within the area. Aspiration of the working area is then performed to removed particles and debris. Aspiration can occur simultaneously with the deactivating of the first occlusive device, if desired. Alternatively, either step can be performed first.

In another aspect of the method of the present invention, the occlusive devices are activated and deactivated more than once. After the first occlusive device is deactivated to allow blood flow into the area, the occlusive device is reactivated. The second occlusive device is then deactivated, to allow blood flow in from the distal end of the working area. The second occlusive device is reactivated, and these steps can be repeated any number of times until sufficient irrigation and aspiration of the working area occurs.

In yet another aspect of the method, the first inner catheter with its occlusive device is delivered into one branch of a bifurcated vessel (such as the carotid artery), while a second inner catheter having a third occlusive device on its distal end is delivered into the other branch of the bifurcated vessel to occlude it. Aspiration then occurs in both branches of the artery to remove particles and debris.

In a further aspect of the method, aspiration occurs through the main catheter, and a separate aspiration catheter is not required. Following removal of the therapy catheter, and deactivation of the first occlusive device to allow blood flow into the working area, aspiration occurs through the distal end of the main catheter. This eliminates the need to deliver a separate aspiration catheter, thus saving time which is critical in these types of procedures.

If desired, an irrigation catheter can be delivered into the working area following the removal of the therapy catheter. The irrigation catheter is used to deliver irrigation fluid to the working area. Aspiration then occurs through the distal end of the main catheter. In this case, anatomical irrigation (the use of the patient's own blood flow for irrigation) as described above, is not used.

Yet another aspect of the method may be performed with a single occlusive device. A main catheter or guide catheter is first delivered into the carotid artery, with the distal end positioned just proximal to the occlusion. An inner catheter having an occlusive device on its distal end is then positioned with the occlusive device distal to the occlusion. The occlusive device is activated to occlude the artery distal to the occlusion. A therapy catheter is delivered into the artery until it reaches the occlusion and therapy is performed to reduce or eliminate the occlusion. The therapy catheter is removed, and an intermediate catheter is delivered to a position proximal to the occlusive device. Preferably, the distance between the proximal end of the occlusive device and the distal end of the intermediate catheter is narrowed at one point during aspiration to a distance of about 2 centimeters or less. The area just proximal to the occlusive device is aspirated, using the intermediate catheter, and then irrigated. The aspirating and irrigating steps can be repeated as often as necessary to facilitate the removal of particles and debris.

In another embodiment, the intermediate catheter has two or more lumens, such that aspiration and irrigation occur through different lumens within the same catheter. This prevents the possibility that aspirated particles will be flushed back into the patient when irrigation is begun.

In further aspects of the present invention, two and even three occlusive devices are employed. In the case of two occlusive devices, a main or guide catheter with an occlusive device on its distal end is delivered to the common carotid artery and the occlusive device is activated. Next, an inner catheter with an occlusive device is delivered distal to the occlusion in the internal carotid artery and activated, thus isolating the occlusion between the two occlusive devices. Therapy is performed on the occlusion, followed by aspiration, and irrigation if desired.

When three occlusive devices are used, an occlusive device is activated in the common carotid artery. An inner catheter with an occlusive device is then delivered to the external carotid artery and the occlusive device activated. Next, a second inner catheter is delivered to the internal carotid artery past the site of the occlusion and the occlusive device activated to occlude the internal carotid artery. Alternatively, the first inner catheter and occlusive device is delivered to the internal carotid artery and activated, followed by delivery and activation of the second inner catheter and occlusive device in the external carotid artery. In either case, the occlusion is completely isolated between the three occlusive devices. This is followed by therapy on the occlusion and sequential aspiration and irrigation as desired.

Accordingly, a carotid artery can be treated quickly and efficiently. The patient's own blood can serve as irrigation fluid, thereby eliminating the need for a separate irrigation catheter and supply of irrigation fluid. The working area may be cleaned in an efficient manner by performing repeated activation and deactivation of the occlusive devices surrounding the working area. The catheter-based approach reduces the amount of time required to complete the procedure, and allows normal blood flow in the vessel to be restored in a very short period of time. Use of a minimally invasive procedure reduces risks and trauma to the patient, decreases costs, and improves recovery time.

Another aspect of the invention comprises a method for the treatment of an occlusion in a branch of a bifurcated blood vessel having a common portion and two branches, such as the carotid artery, comprising providing an elongate member having an occlusive device at a distal end portion thereof, delivering the elongate member through the common portion of the bifurcated vessel and into a branch of the bifurcated vessel (such as the internal carotid artery), and positioning the occlusive device in said branch distal of the occlusion. The method further comprises sliding a therapy catheter on the elongate member, occluding said branch only on the distal side of the occlusion by actuating the occlusive device, treating the occlusion with the therapy catheter, and providing a second catheter having a fluid flow lumen in fluid communication with a fluid flow opening at a distal end portion of the second catheter. The method additionally comprises using the occlusive device to occlude said branch of the vessel while: (a) positioning the fluid flow opening of the second catheter in said branch of the vessel at a location between the occlusive device and the treated occlusion; and (b) applying fluid pressure to the fluid flow lumen to cause fluid flow along said branch, between (i) an intersection of said branch with the common portion and (ii) said location, whereby fluid flows across the treated occlusion; and then deactuating the occlusive device.

Still another aspect of the invention comprises a method for the treatment of an occlusion in a branch of a bifurcated blood vessel having a common portion and two branches, such as the carotid artery, comprising providing an elongate member having an occlusive device at a distal end portion thereof, delivering the elongate member through the common portion of the bifurcated vessel and into a branch of the bifurcated vessel (such as the internal carotid artery), positioning the occlusive device in said branch distal of the occlusion, sliding a therapy catheter on the elongate member, and occluding said branch on the distal side of the occlusion by actuating the occlusive device. The method further comprises treating the occlusion with the therapy catheter, removing the therapy catheter from said branch of the vessel, providing a second catheter having a fluid flow lumen in fluid communication with a fluid flow opening at a distal end portion of the second catheter, and sliding the second catheter on the elongate member after the removal of the therapy catheter. The method additionally comprises using the occlusive device to occlude said branch of the vessel while (a) positioning the fluid flow opening of the second catheter in said branch of the vessel at a location between the occlusive device and the treated occlusion; (b) applying fluid pressure to the fluid flow lumen to cause fluid flow along said branch, between (i) an intersection of said branch with the common portion and (ii) said location, whereby fluid flows across the treated occlusion; and then deactuating the occlusive device.

Yet another aspect of the invention comprises a method for the treatment of an occlusion in a branch of a bifurcated blood vessel having a common portion and two branches, such as the carotid artery, comprising providing an elongate member having an occlusive device at a distal end portion thereof, delivering the elongate member through the common portion of the bifurcated vessel and into a branch of the bifurcated vessel (such as the internal carotid artery), positioning the occlusive device in said branch distal of the occlusion, sliding a therapy catheter on the elongate member, occluding said branch only on the distal side of the occlusion by actuating the occlusive device, and treating the occlusion with the therapy catheter. The method further comprises using the occlusive device to occlude the branch of the vessel while: (a) delivering irrigation fluid to a distal end portion of the therapy catheter through an annulus between the therapy catheter and the elongate member; (b) passing the irrigation fluid out of a fluid flow opening in the distal end portion of the therapy catheter; and (c) positioning the fluid flow opening of the therapy catheter in said branch of the vessel at a location near the occlusive device between the occlusive device and the treated occlusion, such that fluid flows across the treated occlusion; and then deactuating the occlusive device.

Still another aspect of the invention comprises a method for the treatment of an occlusion in a branch of bifurcated blood vessel having a common portion and two branches, such as the carotid artery, comprising providing an elongate member having an occlusive device at a distal end portion thereof, delivering the elongate member through the common portion of the bifurcated vessel and into a branch of the bifurcated vessel (such as the internal carotid artery), positioning the occlusive device in said branch distal of the occlusion, positioning an outer catheter so that a portion of the outer catheter is in the common portion of the vessel, sliding a therapy catheter within the outer catheter and on the elongate member, actuating the occlusive device such that it occludes said branch of the vessel, and treating the occlusion with the therapy catheter. The method further comprises using the occlusive device to occlude the branch of the vessel while (a) delivering irrigation fluid to a distal end portion of the outer catheter; (b) passing the irrigation fluid out of a fluid flow opening in the distal end portion of the outer catheter; (c) positioning the fluid flow opening of the outer catheter in said branch of the vessel at a location between the occlusive device and the treated occlusion, such that fluid flows across the treated occlusion; and then deactuating the occlusive device.

Still another aspect of the invention comprises a method for treatment of an occlusion in a branch of a bifurcated blood vessel having a common portion and two branches, comprising positioning an occlusive device distal of the occlusion to occlude said branch of the vessel, treating the occlusion using a therapy device, delivering irrigation fluid between the occlusion and the occlusive device such that irrigation fluid flows across the treated occlusion towards an intersection of said branch and the common portion, wherein emboli in said branch are carried to the intersection, and allowing anatomical blood flow in the common portion to carry the emboli through another of the branches.

Yet another aspect of the invention comprises a method for the treatment of an occlusion in a blood vessel, such as the carotid artery, comprising providing an inner catheter comprising an elongate member having an occlusive device at a distal end portion thereof, delivering the elongate member through the vessel, positioning the occlusive device distal of the occlusion, sliding a therapy catheter on the elongate member, actuating the occlusive device such that it occludes the vessel, and treating the occlusion with the therapy catheter. The method further comprises uses the occlusive device to occlude the vessel while: (a) delivering irrigation fluid through the elongate member; (b) passing the irrigation fluid out of a fluid flow opening in the occlusive device such that fluid flows across the treated occlusion; and then deactuating the occlusive device. Still another aspect of the invention comprises a method of performing a medical procedure in a blood vessel using an expandable member which seals against walls of the blood vessel in response to application of an expansion force through a range of vessel diameters up to a maximum diameter beyond which sealing will not occur in the vessel, in which the method comprises positioning the expandable member in a selected blood vessel distal to an occlusion to be treated at a location where the vessel diameter is at least 20% less than said maximum diameter, applying an expansion force to cause the expandable member to expand into sealing contact with walls of the selected vessel at said location, and treating the occlusion while the expandable member is expanded, whereby the expandable member seals against walls of the selected vessel even if the diameter of the selected vessel at said location increases to said maximum diameter as a result of the treatment.

Another aspect of the invention comprises a method of treating an occlusion in a blood vessel, comprising positioning an expandable member distal to the occlusion to be treated, performing therapy on the occlusion, and using the expandable member to block migration of emboli created as a result of the therapy, while allowing blood to flow from one side to another side of the expandable member in a proximal to distal direction. The method further comprises positioning a fluid port of a catheter between the treated occlusion and the expandable member, and applying suction to the fluid port to aspirate fluid into the catheter while the fluid port is positioned between the treated occlusion and the expandable member.

Still another aspect of the invention comprises a method of treating an occlusion in a blood vessel, comprising positioning an expandable member distal to the occlusion to be treated, performing therapy on the occlusion, and using the expandable member to block migration of emboli created as a result of the therapy, while allowing blood to flow past the expandable member in a proximal to distal direction. The method further comprises positioning a fluid port of a catheter between the treated occlusion and the expandable member, delivering irrigation fluid through the fluid port, and using the irrigation fluid to provide fluid flow across the treated occlusion in a distal to proximal direction.

Yet another aspect of the invention comprises a method of treating an occlusion in a blood vessel, comprising positioning an expandable member distal to the occlusion to be treated, using a therapy balloon to perform therapy on the occlusion, using the expandable member to block migration of emboli created as a result of the therapy, while allowing blood to flow from one side to another side of the expandable member in a proximal to distal direction. The method further comprises using the therapy balloon to occlude the blood vessel at a location distal to the treated occlusion, positioning a fluid port of a catheter between the treated occlusion and said location, and providing fluid flow through the fluid port such that said fluid flows across the treated occlusion.

BRIEF DESCRIPTION OF THE DRAWINGS

FIG. 5 is a side view of the distal end of an embodiment of an inner catheter.

FIG. 6 is a partial cross-sectional view of the inner catheter taken along line 6—6 of FIG. 5.

FIG. 10 is a side view of an embodiment of a single operator aspiration catheter.

FIG. 11 is a cross-sectional view of the single operator aspiration catheter taken along line 11—11 in FIG. 10.

FIG. 13 is a side view of an embodiment of a single operator irrigation catheter.

FIGS. 14 through 16A are cross-sectional views of the single operator irrigation catheter taken along lines 14—14, 15—15 and 16A—16A of FIG. 13.

FIG. 24 is a perspective view of an embodiment in which the intermediate catheter is used for irrigation of emboli.

FIG. 24A is a perspective view of an embodiment in which a therapy catheter is used for irrigation of emboli.

DETAILED DESCRIPTION OF THE PREFERRED EMBODIMENT

The preferred embodiments of the present invention provide improved methods for containing and removing emboli resulting from plaque, thrombi or other occlusions. The preferred methods are particularly advantageous for use in the carotid artery and other arteries above the aortic arch. The preferred methods may be used, for example, in the treatment of a stenosis or an occlusion which has a length and a width or thickness resulting in at least partial occlusion of the vessel's lumen. Thus, the preferred methods are effective in treating both partial and substantially complete occlusions of arteries. It is to be understood that "occlusion" as used herein, includes both complete and partial occlusions, stenoses, emboli, thrombi, plaque, and any other substance which at least partially occludes the lumen of the artery. Although the methods disclosed herein are described with specific reference to the carotid arteries, they can be applied to other vessels as well, particularly bifurcated vessels.

Figure 1:
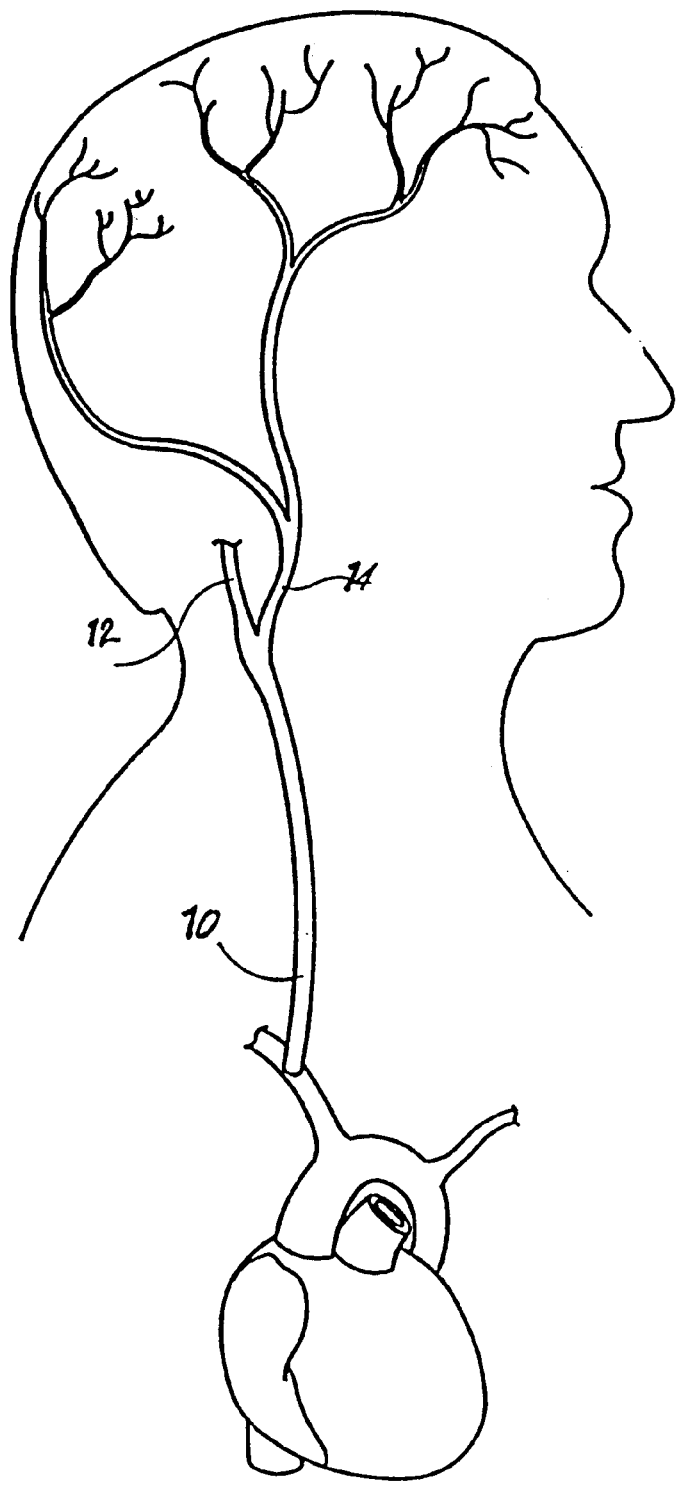
FIG. 1 is a perspective drawing of the carotid arteries.

As illustrated in FIG. 1, the common carotid artery 10 is located in the neck and branches off into the internal carotid 12, and the external carotid 14 arteries. The internal carotid artery 12 supplies blood to the brain, while the external carotid artery 14 supplies blood to the head and face. The preferred methods of the present invention will be described for the treatment of an occlusion within the internal carotid artery. It is to be understood that this method can be used on other arteries as well.

Generally, the preferred methods are adapted for the percutaneous treatment, containment and removal of occlusions within the carotid arteries or other arteries above the aortic arch. In one of these methods, a main catheter having an occlusive device on its distal end is first delivered to the common carotid artery, proximal to the site of the occlusion. It should be noted that, as used herein, "proximal" refers to the portion of the apparatus closest to the end which remains outside the patient's body, and "distal" refers to the portion closest to the end inserted into the patient's body. The occlusive device is activated to stop the downstream flow of blood. Collateral pressures from the Circle of Willis and other vessels keep the blood flow in the direction of the main catheter, preventing any emboli from moving downstream. In another embodiment, a main catheter without an occlusive device on its distal end, or a main catheter having an occlusive device which is not deployed, is delivered to the common carotid artery, proximal to the site of the occlusion.

In either case, an inner catheter having an occlusive device on its distal end is delivered through the main catheter and across the site of the occlusion. Alternatively, a detachable occlusive device can also be used. In either case, the occlusive device is activated at a site distal to the occlusion.

In some cases, a second inner catheter is used to provide a third occlusive device. One inner catheter is delivered to the internal carotid artery, while the other inner catheter is delivered to the external carotid artery. When activated, the three occlusive devices completely isolate the area surrounding the occlusion to be treated.

A therapy catheter is then delivered to the site of the occlusion to treat the occlusion. Such treatment includes, but is not limited to, balloon angioplasty, thermal balloon angioplasty, delivery of an intravascular stent, atherectomy, or radiation treatment.

In one embodiment of the present invention, once therapy is complete, an irrigation catheter is delivered into the working area to provide irrigation fluid. Alternatively, anatomical irrigation can be used, as explained below. Aspiration of the area surrounding the treated occlusion is begun using either the main catheter or a separate aspiration catheter. Blood flow is allowed into the working area to be aspirated by deactivating the occlusive devices on the main and/or inner catheters. This helps to irrigate the area and ensure the removal of particles and debris from the artery.

In another embodiment of the present invention, the need for a separate irrigation catheter and irrigation fluid are eliminated. In the context of removing plaque, thrombi or other blockages from blood vessels, separate irrigation fluid is generally provided through an irrigation catheter to the site of treatment. It has been discovered that the patient's own blood can be used as irrigation fluid, without the need for delivery of a separate irrigation catheter and irrigation fluid.

Although the patient's own flow of blood can provide an irrigation source, situations sometime arise where providing separate irrigation fluid is desired. In such cases a separate catheter is introduced into the patient after the therapy catheter is removed and is delivered within close proximity to the occlusive device. Once the catheter is delivered proximal to the occlusive device, the area is first aspirated through the catheter. By delivering the catheter close to the occlusive device a turbulence is created freeing debris from the edge of the occlusive device and other areas where it may be trapped. The debris is then aspirated from the patient. Following aspiration, irrigation fluid is provided if desired to flush any remaining particles and debris from the internal carotid.

Main Catheter

In the preferred methods, a main or guide catheter is first introduced into the patient's vasculature. This catheter is used to guide the insertion of other catheters and devices to the desired site. A guide catheter (e.g., 9F) or a long sheath (e.g., 7F) may be used as the main catheter. If the guide catheter is not sufficiently stiff, then an angiography catheter may be positioned inside the guide catheter, and both the guide catheter and the angiography catheter can be delivered on a guidewire. (The term guidewire is used broadly herein to include elongate members (such as hollow or tubular members) made of metal as well as other materials, such as plastic.) Once the guide catheter is properly positioned, the angiography catheter can be removed. In some embodiments of the present invention, the main catheter has an occlusive device on its distal end. The occlusive device can be an inflatable balloon, filter, expandable braid or other mechanical occlusive device. The occlusive device should be capable of preventing the migration of particles and debris from the working area, either through total or partial occlusion of the vessel. Note that the occlusion of the vessel need not be complete, and that substantial occlusion of the vessel may be sufficient. The catheter should be sized so as to slidably receive the inner, therapy and intermediate (irrigation and/or aspiration) catheters inserted therethrough.

Figure 2:
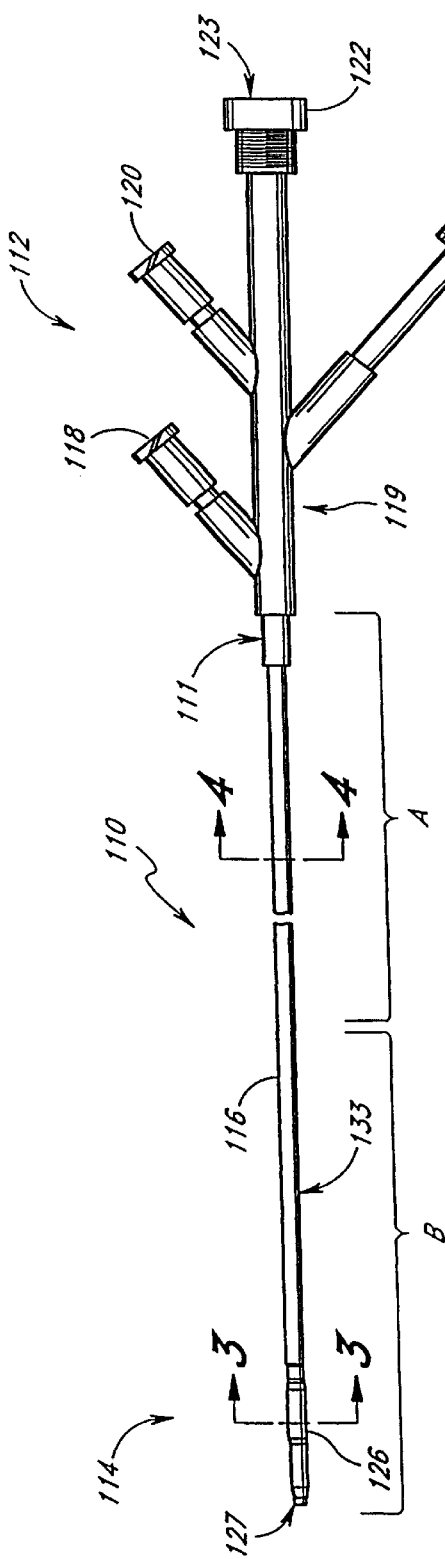
FIG. 2 is a side view of an embodiment of a main catheter.
Figure 4:
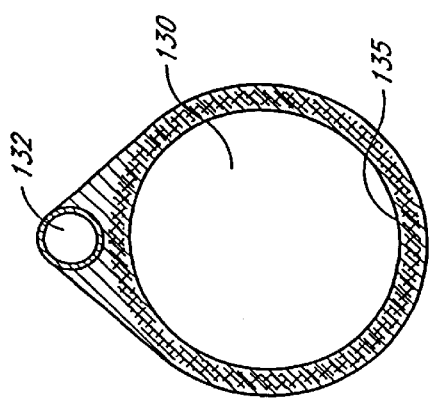
FIG. 4 is a cross-sectional view of the main catheter taken along line 4—4 of FIG. 2.
Figure 3:
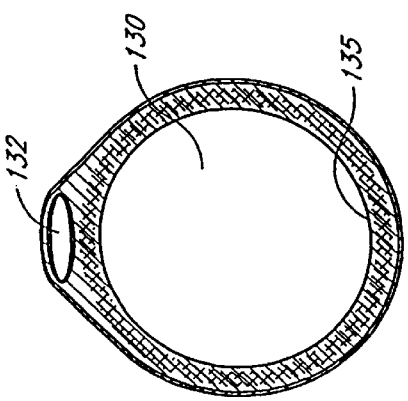
FIG. 3 is a cross-sectional view of the main catheter taken along line 3—3 of FIG. 2.

FIG. 2 illustrates a side view of a catheter which can be used as the outer or main catheter of the present system. Catheter 110 generally comprises an elongate flexible tubular body 116 extending between a proximal control end 112 and a distal functional end 114. The tubular body 116 has a main lumen 130 which extends between the ends 112 and 114. The main lumen 130 terminates in a proximal opening 123 and a distal opening 127. A smaller inflation lumen 132, configured in a side-by-side relationship with the main lumen 130, extends along the length of the tubular body 116, and terminates within an occlusive device such as an occlusion balloon 126 mounted on the distal end 114 of the catheter 110, as described below. The inflation lumen 132, illustrated in FIGS. 3 and 4, is in fluid communication with the occlusion balloon 126, such that fluid passing through the inflation lumen 132 may be used to inflate or deflate the balloon 126. The proximal end of the inflation lumen can terminate at one of the ports 122, 124 on the proximal end of the catheter 110.

A control manifold 119 is provided at the proximal end 112 of the catheter 110. The control manifold 119 is generally provided with a number of ports to provide access to the catheter lumen 130. For example, for the embodiment depicted in FIG. 2, the control manifold 119 is provided with a catheter end-access port 122 and a catheter side-access port 124, to provide an introduction point for the insertion of other catheters into the lumen 130. Ports 122 and 124 are preferably provided with standard Touhy Borst connectors, although other types of connectors may be used. An inflation port 118, in fluid communication with the small inflation lumen 132, is further provided on the manifold 119 for attachment of devices to inflate or deflate the occlusion balloon 126. The manifold 119 is also provided with an irrigation/aspiration port 120 which is in fluid communication with the lumen 130, for attachment of devices to provide irrigation fluid or aspiration pressure. Other embodiments of the main catheter 110 may feature more or less ports, depending upon the number of lumens in the catheter and the desired functionalities of the catheter.

The manifold 119 is preferably formed out of hard polymers or metals, which possess the requisite structural integrity to provide a functional access port to the catheter lumen, such as for balloon inflation or delivery of irrigation fluid and/or aspiration pressure. In one preferred embodiment, the manifold 119 is integrally formed out of polycarbonate. Of course, any suitable material may be used to form the manifold 119, including acrylonitrile butadiene styrene (ABS).

As illustrated in FIG. 2, an inflatable balloon 126 is mounted on the distal end 114 of the catheter 110. The inflatable balloon 126 will function as an occlusion balloon, to prevent blood and debris from passing through the blood vessel distal to the balloon 126. Thus, the inflatable balloon 126 is preferably able to expand to fit a variety of different blood vessel diameters. Accordingly, it is preferred that the inflatable balloon 126 have a compliant expansion profile, tending to increase in radial diameter with increasing inflation pressure. To achieve this, the balloon 126 may be made out of materials which impart such expansion characteristics, including elastomeric materials such as latex or irradiated polyethylene. In one preferred embodiment, the inflatable balloon 126 is formed out of a material comprising a block copolymer of styrene-ethylene-butylene-styrene, sold under the trade name C-FLEX. Non-compliant balloons, such as those made from PET can also be used. Further details as to balloons of this type are disclosed in our copending application entitled "Pre-Stretched Catheter Balloon", Ser. No. 08/812,140, filed Mar. 6, 1997, now U.S. Pat. No. 5,868,705, the entirety of which is incorporated by reference.

Figure 19:
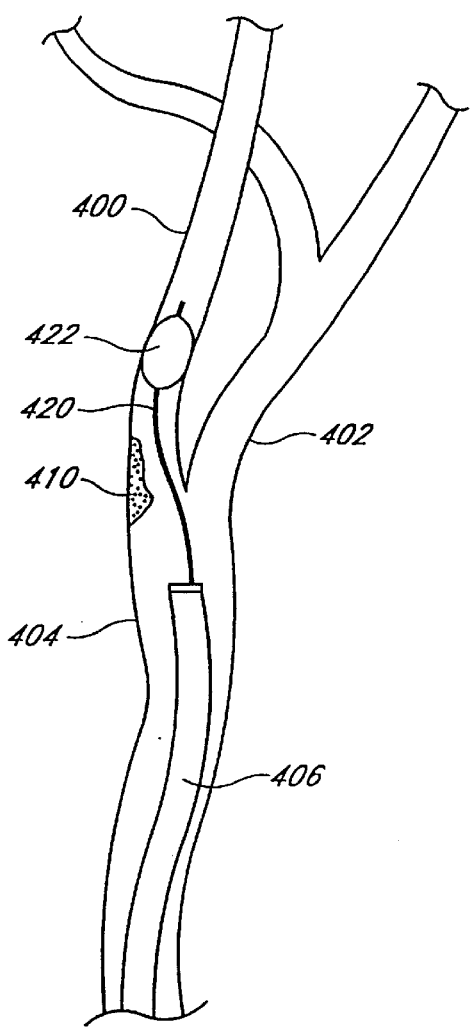
FIG. 19 is a perspective view of yet another example of an emboli containment and removal method which employs a single occlusive device.
Figure 20:
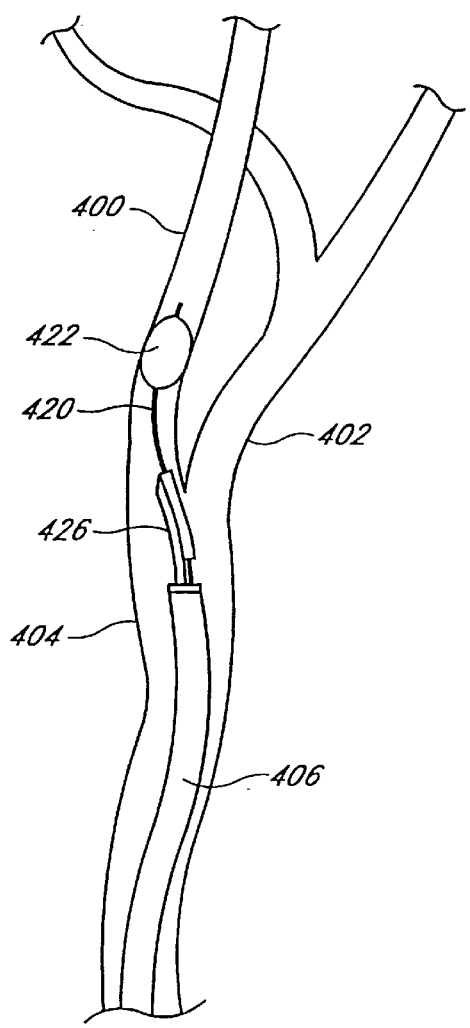
FIG. 20 is a perspective view of the emboli containment and removal method illustrated in FIG. 19, showing the use of an intermediate catheter.

Alternatively, as illustrated in FIGS. 19–20, the main catheter 406 does not include a distal occlusive device, or the distal occlusive device on the main catheter is not used.

Inner Catheter

An inner catheter or guidewire having an occlusive device on its distal end is preferably made of metals such as stainless steel or nitinol, or plastics or composites. The preferred methods can be effectively carried out using any of a number of guidewires or catheters that perform the function of occluding the vessel and allowing for the slidable insertion of various other catheters and devices. The term "catheter" as used herein is therefore intended to include both guidewires and catheters with these desired characteristics.

A preferred inner catheter is illustrated in FIGS. 5 and 6. The catheter apparatus 310 is generally comprised of four communicating members including an elongated tubular member 314, an inflatable balloon member 316, a core-wire member 320 and a coil member 322. The catheter apparatus 310 is preferably provided with an outer coating of a lubricous material, such as TEFLON.

The body member 314 of the catheter apparatus 310 is in the form of hypotubing and is provided with proximal and distal ends 314A and 314B as well as an inner lumen 315 extending along the tubular member 314. The balloon member 316 is coaxially mounted on the distal end 314B of the tubular member 314 by suitable adhesives 319 at a proximal end 316A and a distal end 316B of the balloon member 316 as in the manner shown in FIG. 6. The core-wire member 320 of the catheter 310 may be comprised of a flexible wire 320. The flexible wire 320 is joined by adhesives, soldering, brazing or crimping at a proximal end 320A of the flexible wire 320 to the distal end 314B of the tubular member 314 as in the manner show in FIG. 6.

Preferably, the proximal end 320A of the flexible wire 320 has a transverse cross sectional area substantially less than the smallest transverse cross-sectional area of the inner lumen 315 of the tubular member 314. In the preferred embodiment, the flexible wire 320 tapers in the distal end 320B to smaller diameters to provide greater flexibility to the flexible wire 320. However, the flexible wire may be in the form of a solid rod or a ribbon or combinations thereof.

As shown in FIG. 6, the distal end 320B of the flexible wire 320 is secured to a rounded plug 318 of solder or braze at the distal end 322B of the coil member 322. The coil member 322 of the catheter 310 may be comprised of a helical coil 322. The coil member 322 is coaxially disposed about the flexible wire 320, and is secured to the flexible wire 320 by soldering, brazing or adhesives at about the proximal end 320A of the flexible wire 320 as in the manner shown in FIG. 6.

The balloon member 316 is preferably a compliant balloon formed of a suitable elastic material such as a latex or the like, but can be made of non-compliant materials as well. The flexible coil 322 is preferably formed of a wire of platinum based alloys or gold. The flexible core-wire 320 and the tubular member 314 are preferably formed of a nickel-titanium alloy or stainless steel.

Once the inner catheter has been properly positioned inside the carotid artery at a point distal to the occlusion, the occlusive device at the distal end of the inner catheter is actuated to occlude the vessel distal to the existing occlusion to create a working area. When a detachable occlusive device is used, the occlusive device is positioned at a point distal to the occlusion to be treated, and activated to occlude the artery. It is to be understood that the stenosis or occlusion could be in a discrete location or diffused within the artery. Therefore, although placement of the occlusive device is said to be distal to the stenosis or occlusion to be treated, portions of the diffused stenosis or occlusion may remain distal to the occlusive device.

Therapy Catheter

After the area surrounding the occlusion has been isolated, a therapy catheter then is delivered to the site of the occlusion. The term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Thrombectomy devices can be used, as can rheolitic devices, and devices which create a venturi effect within the artery. Various thrombolytic or other types of drugs can be delivered locally in high concentrations to the site of the occlusion. It is also possible to deliver various chemical substances or enzymes via a catheter to the site of the stenosis to dissolve the obstruction. The term "therapy catheter" encompasses these and similar devices.

Aspiration and Irrigation Catheters

After the therapy has been performed and the occlusion has been treated, the working area may be aspirated to remove fluid and debris. Aspiration can be provided through the main catheter if desired. A source of negative pressure is attached at the proximal end of the main catheter, and fluid and debris are aspirated through the main catheter's main lumen. Alternatively, an aspiration catheter or similar debris removing device can be delivered to the working area to remove particles and any other debris. The term "aspiration catheter" includes any device which creates an area of fluid turbulence and uses negative pressure to aspirate fluid and debris, and includes thrombectomy catheters, rheolitic devices and those devices which create a venturi effect within the vessel. Thus, it is possible that a single catheter is used as both the therapy catheter and the aspiration catheter.

Figure 7:
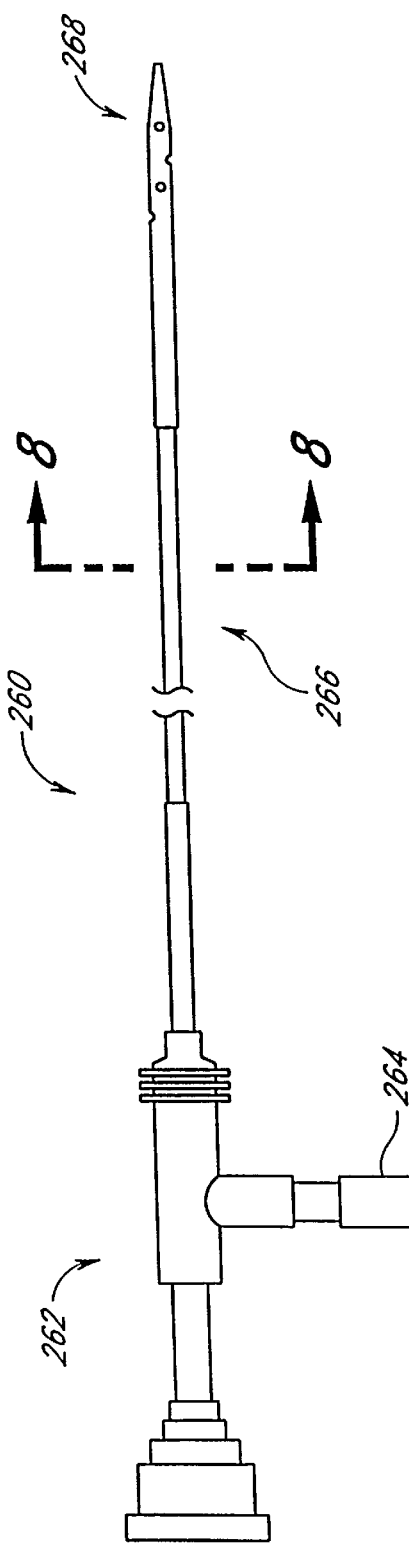
FIG. 7 is a side view of an embodiment of an over-the-wire aspiration catheter.

An aspiration catheter particularly suited for use with the preferred methods is illustrated in FIG. 7. The catheter 260 includes an adapter 262 and a seal at its proximal end. The catheter 260 further includes an aspiration port 264 to which a source of negative pressure is attached. The aspiration catheter further comprises a long hollow shaft 266 having a distal end 268. The distal tip 268 can/include a radiopaque marker to aid in locating the tip 268 during insertion into the patient, and is preferably soft to prevent damage to the patient's vasculature.

Figure 9:
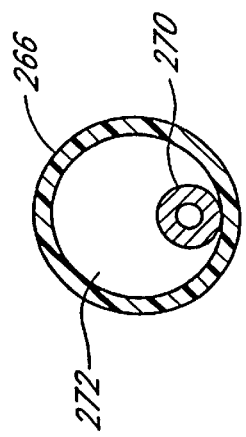
FIG. 9 is a cross-sectional view of the over-the-wire aspiration catheter taken along line 8—8 in FIG. 7, showing an elongate member (e.g., a guidewire) inserted therethrough.
Figure 8:
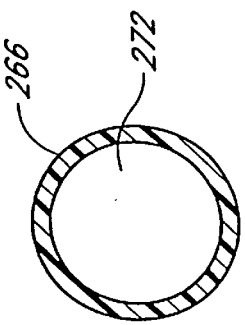
FIG. 8 is a cross-sectional view of the over-the-wire aspiration catheter taken along line 8—8 in FIG. 7.

The aspiration catheter illustrated in FIG. 7 is an over-the-wire catheter. As seen in FIG. 8, the catheter shaft 266 is hollow. During insertion of the aspiration catheter 260, the proximal end of a guidewire 270 is inserted into the distal end of the aspiration catheter 268, and the aspiration catheter 260 is slidably advanced over the guidewire 270, which is positioned inside the hollow lumen 272 of the aspiration catheter 260. The position of the guidewire 270 relative to the shaft 260 of the aspiration catheter 260 is illustrated in FIG. 9, but of course, can vary. For this type of aspiration catheter 260, a very long guidewire 270, generally around 300 centimeters in length, is used to facilitate the insertion of the aspiration catheter 260 over the guidewire 270.

Alternatively, the aspiration catheter 280 can be of a single operator design, as illustrated in FIGS. 10–11. The catheter 280 has an adapter and an aspiration port at its proximal end. Like the over-the-wire aspiration catheter 260 the single operator aspiration catheter 280 further comprises a long hollow shaft 282 having a distal end 288. The distal tip 288 can include a radiopaque marker to aid in locating the tip 288 during insertion into the patient, and is preferably soft to prevent damage to the patient's vasculature. At the distal end of the shaft 288, a guidewire lumen 286 is attached. This lumen 286 provides a separate lumen, apart from the main aspiration lumen 284 of the catheter 280, for the insertion of the guidewire. This guidewire lumen 286 can be as short as 5 centimeters or longer. As illustrated in FIG. 11, during delivery of the aspiration catheter 280, the proximal end of the guidewire is inserted into the distal end of the guidewire lumen 286, and the guidewire lumen 286 is slidably advanced over the guidewire. Unlike the over-the-wire catheter 260 described above, only a short segment of the single operator aspiration catheter 280 rides over the guidewire, and the guidewire remains in the guidewire lumen 286 and does not enter the aspiration lumen 284 of the aspiration catheter 280. With the single operator system 280, the long guidewire used with the over-the-wire catheter 260, and the extra operator needed to handle it, are not required.

Although the guidewire lumen 286 is shown in FIG. 10 as being located only on the distal end 288 of the shaft of the aspiration catheter 280, the lumen 286 can also be made to extend the entire length of the shaft 280 if desired. In both embodiments, the aspiration lumen 284 is advantageously left completely unobstructed to provide more efficient aspiration. The guidewire lumen 286 can also include a slit in the outside wall of the lumen to facilitate faster and easier insertion and removal of the guidewire through the side wall of the lumen.

In another embodiment not shown, the aspiration catheter can be configured such that the therapy catheter can be inserted through the lumen of the aspiration catheter. The lumen is made large enough to accommodate the desired therapy catheter. This allows the aspiration catheter and the therapy catheter to be delivered into the patient at the same time. When therapy is complete, the therapy catheter is removed while the aspiration catheter remains in place. This eliminates the need to separately deliver the aspiration catheter after removal of the therapy catheter, saving valuable time.

In yet another embodiment, also not shown, the therapy catheter can be built over the aspiration catheter. For example, a dual or triple lumen catheter having a dilatation balloon at its distal end can be used. One lumen is used to inflate the dilatation balloon to be used for angioplasty, while the second lumen is used for aspiration. The third lumen is used as a guidewire lumen. Alternatively, the aspiration catheter can be designed to deploy a stent within the occluded artery, or could include an atherectomy device on its distal end. These designs allows a single combined aspiration catheter and therapy catheter to be delivered into the patient. When therapy is complete, aspiration is carried out without the need to first remove the therapy catheter or separately deliver an aspiration catheter.

Figure 12:
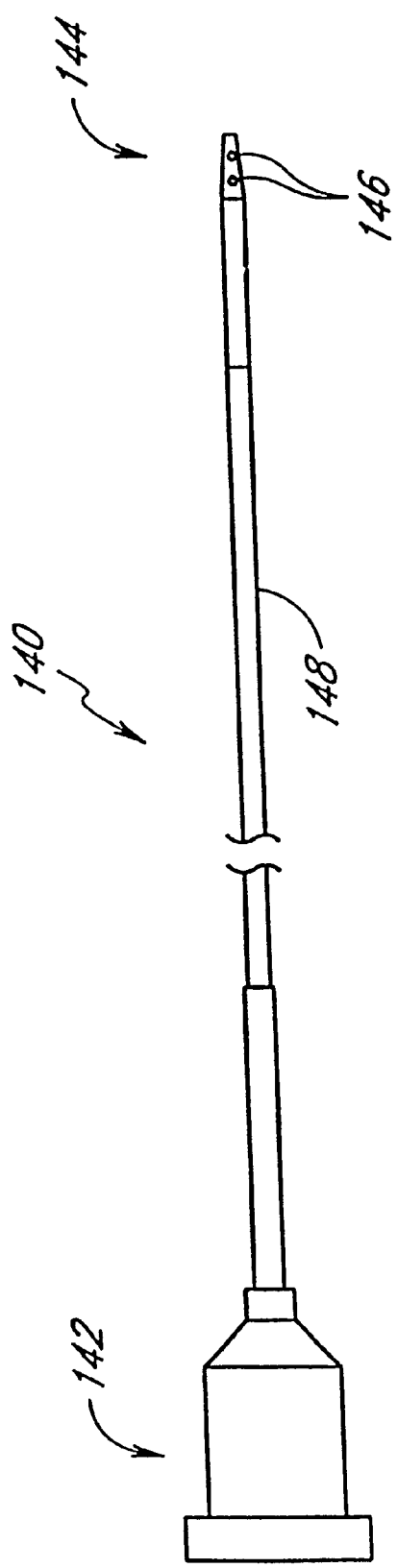
FIG. 12 is a side view of an embodiment of an over-the-wire irrigation or aspiration catheter.

FIG. 12 is a side view of an irrigation catheter 140 or aspiration catheter which may be utilized in the preferred methods. It should be understood that when an irrigation catheter is used, aspiration occurs through the outer pathway between the irrigation and main catheters, while irrigation occurs through the irrigation pathway. Similarly, when an aspiration catheter is used, aspiration occurs through the aspiration catheter while irrigation occurs through the pathway between the aspiration and main catheters. Irrigation fluid is supplied under pressure at the proximal end of the catheter 142 and delivered through the side holes 146 and through the distal end of the catheter 144. Alternatively, aspiration can be provided at the proximal end of the catheter 142 and fluid and debris aspirated through the side holes 146 and through the distal end of the catheter 144. The catheter 140 can be about 125 centimeters in length and constructed from a plastic material such as HYTREL tubing or high density polyethylene (HDPE) or PEBAX (Atochem, France). In order to achieve a softer distal section, the durometer of the tube 148 material is reduced in the distal section to about 55 whereas that of the proximal section 142 is higher, such as about 80. Proximal valves and fittings which are well known in the art can be mounted on the catheter 140 of FIG. 12.

FIGS. 13–16 illustrate another type of irrigation or aspiration catheter 230, a single operator catheter, which can be used in the present system. In the case of the irrigation catheter, irrigation is through the inner pathway and aspiration is through the outer pathway. If the catheter is used for aspiration, aspiration is through the inner pathway and irrigation is through the outer pathway. As shown in FIGS. 13–16, the catheter 230 has an adaptor 232 on its proximal end. This single operator catheter 230 further comprises a long tubular body 236 having a distal end 238. The distal tip 238 can include a radiopaque marker to aid in locating the tip 238 during insertion into the patient, and is preferably soft to prevent damage to the patient's vasculature. At the distal end of the shaft 238, an inner catheter lumen 240 is attached. This lumen 240 provides a separate lumen, apart from the main irrigation or aspiration lumen 242 of the catheter 230, for the insertion of the inner catheter, and has an inner diameter sized to received the inner catheter. In a preferred embodiment, the inner diameter of the lumen is about 0.016" to about 0.020", and more preferably is about 0.019". This inner catheter or guidewire lumen can be as short as 5 centimeters, but can extend 30 centimeters or longer in a proximal direction. During delivery of the catheter 230, the proximal end of the inner catheter is inserted into the distal end of the inner catheter lumen 240, and the lumen 240 is slidably advanced over the inner catheter. Only a short segment of the single operator catheter 230 rides over the inner catheter, and the inner catheter remains in the lumen 240 and does not enter the main lumen 242 of the catheter 230.

Although the inner catheter lumen 240 is shown in FIG. 13 as being located only on the distal end 238 of the shaft of the catheter 236, the lumen 240 can also be made to extend the entire length of the shaft 236 if desired. In both embodiments, the main lumen 242 is advantageously left completely unobstructed to provide more efficient irrigation or aspiration. As seen in FIG. 16, the inner catheter lumen 240 can also include a slit 241 or weakened area in the outside wall of the lumen 240 along the entire length of the lumen 240 to facilitate faster and easier insertion and removal of the inner catheter through the side wall of the lumen 240. By inserting and removing the inner catheter through the side wall of the lumen 240 on the catheter 236, the need to remove adapters and attachments from the proximal end prior to slidably advancing or removing the catheter 236 over the inner catheter is eliminated. It should be understood that this slit 241 or weakened area through which the inner catheter can be inserted and removed can exist on the intermediate catheter regardless of whether the catheter is used for irrigation, aspiration, therapy or some other purpose.

In another embodiment, not shown, the irrigation and aspiration are conducted through a multi lumen catheter. In this embodiment, a single catheter is used. The catheter includes at least two separate lumens; one lumen is used for aspiration and has a source of negative pressure attached at the proximal end, while a second lumen is used to provide irrigation and has a source of irrigation fluid attached at the proximal end.

Additional details relative to the catheters described above are found in copending application Ser. No. 08/813,023, entitled "Catheter for Emboli Containment", filed on Mar. 6, 1997, now U.S. Pat. No. 6,270,477, Ser. No. 08/812,140, entitled "Prestretched Catheter Balloon", filed on Mar. 6, 1997, now U.S. Pat. No. 5,868,705, Ser. No. 08/813,808, entitled "Aspiration Catheter", filed on Mar. 6, 1997, now abandoned, and Ser. No. 08/812,876, entitled "Hollow Medical Wires and Methods of Constructing Same", filed on Mar. 6, 1997, now U.S. Pat. No. 6,068,623, all of which are hereby incorporated by reference.

Preferred Methods

A. Dual Balloon System

Figure 17:
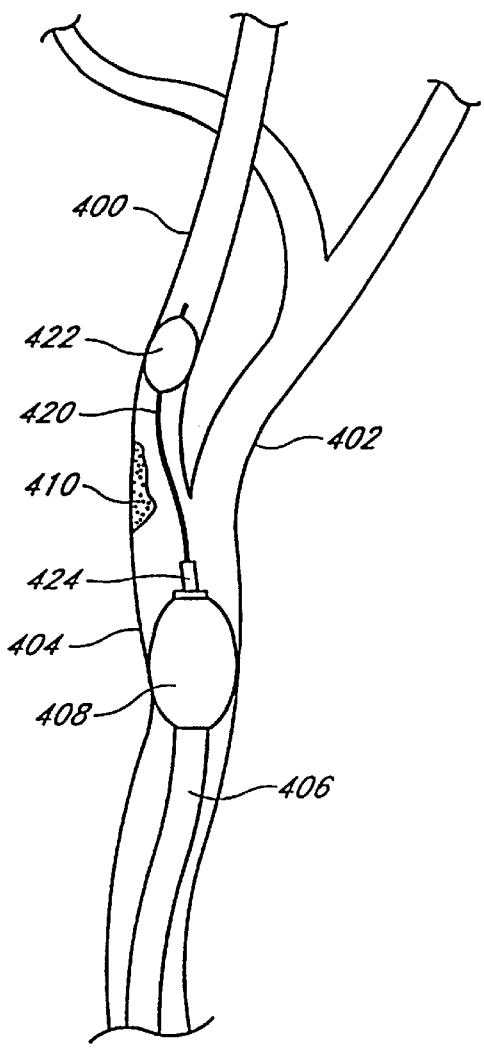
FIG. 17 is a perspective view of one example of an emboli containment and removal method within a carotid artery.

FIG. 17 illustrates the removal of plaque and any associated thrombi from the internal carotid artery 400. It should be noted that this method is merely exemplary, and that occlusions in other locations, such as within the external carotid 402, common carotid 404 artery, or other arteries above the aortic arch, may be treated.

A main catheter or guide catheter 406 is introduced into the patient's vasculature through an incision in the femoral artery in the groin of the patient, or through direct access to the arteries in the neck (e.g., jugular access, in which case the catheters do not need to be as long as in the case of femoral access). The main catheter 406 has a lumen sized to receive other catheters and devices, and can be used to guide the insertion of these other catheters and devices. The main catheter 406 is guided through the vasculature until it reaches the common carotid artery 404, where it can remain in place throughout the procedure. Fluoroscopy is typically used to guide the main catheter 406 and other devices to the desired location within the patient. The devices are frequently marked with radiopaque markings to facilitate visualization of the insertion and positioning of the devices within the patient's vasculature.

Once the main catheter 406 is in place, with its occlusive device 408 at a position proximal to the occlusion 410, the occlusive device 408 is activated. Downstream blood flow is effectively stopped, and blood flow coming from collateral blood vessels distal to the occlusive device prevents the downstream migration of any free particles. In this example, the occlusive device 408 is an inflatable balloon. The balloon is inflated to occlude the common carotid artery 404.

Next, an inner catheter or guidewire 420 having an occlusive device 422 at its distal end is delivered through the main catheter 406 into the internal carotid artery 400 and past the site of the occlusion 410. Alternatively, a detachable occlusive device can be deployed at the site distal to the occlusion, and the delivery device removed. In this example, the occlusive device 422 is also an inflatable balloon. The balloon is inflated to occlude the internal carotid artery at a site distal to the occlusion 410. It should be understood that the occlusion within the artery can be in a discrete location or diffused within the vessel. Therefore, although placement of the distal occlusive device is said to be distal to the occlusion to be treated, portions of the diffuse occlusion may remain distal to the occlusive device.

A working area is therefore created between the two occlusive devices 408, 422 surrounding the occlusion 410. A therapy catheter (not shown) is then delivered. The therapy catheter can be any of a number of devices, including a balloon catheter used to perform angioplasty, a catheter which delivers a stent, a catheter for delivering enzymes, chemicals, or drugs to dissolve and treat the occlusion, an atherectomy device, a thrombectomy device, a rheolitic device, a device which creates a venturi effect within the artery, or a laser or ultrasound device used to ablate the occlusion.

Once the desired therapy is performed, the therapy catheter is withdrawn from the patient's body and an aspiration catheter 424 is delivered through the main catheter 406, preferably over the inner catheter or guidewire 420. The aspiration catheter 424 rides over the guidewire 420 with the guidewire 420 inserted through the aspiration lumen of the catheter 424. Alternatively, a single operator type aspiration catheter can be used, in which only a portion of the aspiration catheter rides over the guidewire, which is inserted into a separate guidewire lumen. FIG. 17 illustrates the treatment site after the over-the-wire aspiration catheter 424 is inserted into the internal carotid artery 400.

After the aspiration catheter 424 is in place, aspiration is begun. A source of negative pressure is connected to the aspiration catheter 424 at its proximal end. A preferred source of negative pressure is any container containing a fixed vacuum, such as a syringe, attached to the proximal end of the aspiration catheter 424 at the aspiration port. A mechanical pump or bulb or any other appropriate source of negative pressure can also be used, including the creation of a venturi effect within the blood vessel. The difference between the existing pressure within the vessel and the aspiration or negative pressure within the vessel should not exceed about 50 psi. If too much aspiration is applied, the change in pressure in the vessel will be too great and damage may occur to the vessel itself.

Prior to aspiration, simultaneous with aspiration, or after aspiration is begun, the proximal occlusive device 408 is deactivated to allow blood flow into the area. The blood flow into the area provides irrigation fluid which creates turbulence and facilitates the removal of particles and debris. Preferably, the anatomical irrigation pressure provided is approximately 1–1.5 psi, and the blood flow into the area is at least 10 cubic centimeters/min and more preferably about 60–80 cubic centimeters/min. In a preferred embodiment, the proximal occlusive device is then reactivated, and the distal occlusive device is deactivated. This allows blood flow into the working area from the distal end. Following aspiration, the distal occlusive device is reactivated. This method of alternately deactivating and reactivating the occlusive devices acts to contain and direct the emboli to an area within the working area where they will be aspirated. Particles are initially contained between the two occlusive devices. When the proximal occlusion device is deactivated, blood flow forces particles and debris toward the distal end of the working area. The working area is aspirated, and the occlusive device reactivated. When the distal occlusive device is deactivated, blood flow forces particles and debris back toward the proximal end of the working area, where they are then aspirated. The steps of deactivating and reactivating the occlusive devices and aspirating the working area can be repeated as often as desired, until the working area is substantially free of particles and debris.

When the deactivating and reactivating of the occlusive devices and aspiration steps are complete, the aspiration catheter is removed, and the occlusive devices are deactivated. The main and inner catheters are also removed from the patient.

As described above, the aspiration catheter can be sized such that it can receive the therapy catheter within its lumen. In this case, the aspiration catheter and the therapy catheter are delivered into the artery together. When therapy is complete, the therapy catheter is removed while the aspiration catheter remains in place. When aspiration is complete, the aspiration catheter, inner catheter and main catheter are removed from the patient's body. Delivering the aspiration catheter and therapy catheter together saves time, which is critical during these types of procedures.

In yet another embodiment, aspiration takes place through the lumen of the inner catheter or guidewire. The occlusive device on the inner catheter is positioned distal to the occlusion, and the occlusive device is activated to at least partially occlude the vessel. The therapy catheter is delivered and therapy performed. A source of negative pressure is provided at the proximal end of the inner catheter, and aspiration occurs through openings located at the distal end of the catheter just proximal to the occlusive device. This eliminates the need for a separate aspiration catheter, and the need to remove the therapy catheter prior to aspiration. Again, this saves time, which is critical during these types of procedures.

B. Triple Balloon System

Figure 18:
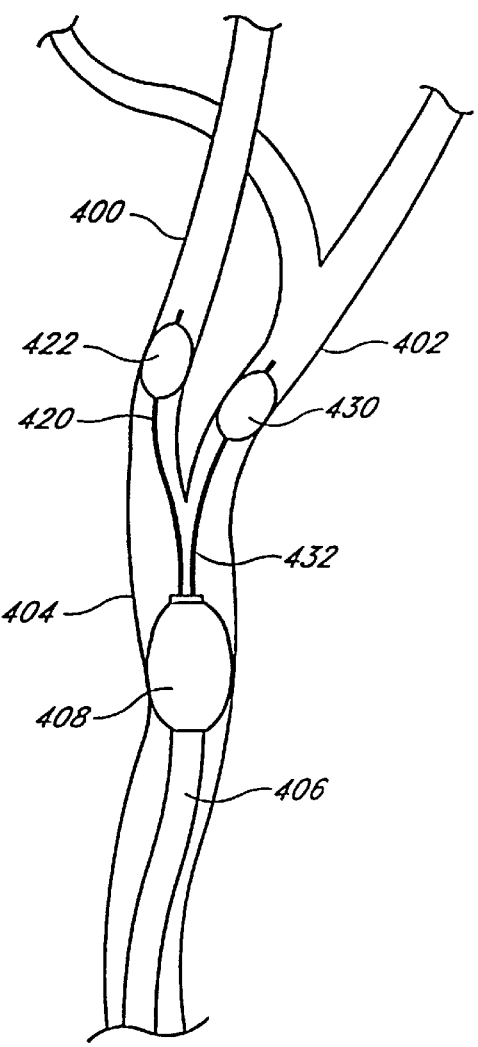
FIG. 18 is a perspective view of another example of an emboli containment and removal method.

In another embodiment illustrated in FIG. 18, a third occlusive device 430 is used to occlude the external carotid artery 402. Once the main catheter 406 is in place and the common carotid artery 404 is occluded, inner catheters 420, 432 are delivered to both the internal 400 and external 402 carotid artery branches and occluded. Following therapy and aspiration of the internal carotid artery 400, the aspiration catheter is moved in a proximal direction, and delivered over the inner catheter 420 into the external carotid artery branch 402. Aspiration is then performed in that branch to remove any particles or debris that may have been moved into the external carotid artery 402. The three occlusive devices can be alternately deactivated and reactivated as described above, to ensure the desired clearance of the working area. When aspiration is complete, the occlusive devices are deactivated, and the main 406, aspiration, and inner catheters 420, 432 are removed from the patient.

Should it be desired that a separate irrigation catheter be used to provide irrigation fluid, an irrigation catheter can be delivered to the site of the occlusion following therapy and removal of the therapy catheter. The irrigation catheter is delivered through the main catheter and over the inner catheter. Irrigation fluid is provided through the irrigation catheter, while aspiration is provided through the main catheter.

C. Single Balloon System

In another embodiment illustrated in FIG. 19, only a single occlusive device is used. As described above, a main catheter 406, with or without a distal occlusive device, is introduced into the patient's vasculature through an incision in the femoral artery in the groin of the patient or through direct access to the arteries in the neck. The main catheter 406 is guided through the vasculature until it reaches the common carotid artery 404, where it can remain in place throughout the procedure.

Once the main catheter 406 is in place proximal to the occlusion 410, an inner catheter or guidewire 420 having an occlusive device 422 at its distal end is delivered through the main catheter 406 into the internal carotid artery 400 and past the site of the occlusion 410. Alternatively, a detachable occlusive device can be deployed at the site distal to the occlusion, and the delivery device removed. In this example, the occlusive device 422 is an inflatable balloon. The balloon is inflated to occlude the internal carotid artery 400 at a site distal to the occlusion 410. As noted before, it should be understood that the occlusion within the artery can be in a discrete location or diffused within the vessel. Therefore, although placement of the distal occlusive device is said to be distal to the occlusion to be treated, portions of the diffuse occlusion may remain distal to the occlusive device.

A therapy catheter, not shown, is then delivered. Again, the therapy catheter can be any of a number of devices, including a balloon catheter used to perform angioplasty, a catheter which delivers a stent, a catheter for delivering enzymes, radiation, chemicals, or drugs to dissolve and treat the occlusion, an atherectomy device, a thrombectomy device, a rheolitic device, a device which creates a venturi effect within the artery, or a laser or ultrasound device used to ablate the occlusion.

Once the desired therapy is performed, the therapy catheter is withdrawn from the patient's body and an intermediate catheter 426 is delivered through the main catheter 406. A single operator type catheter may be used in which only a portion of the catheter rides over the guidewire, which is inserted into a separate guidewire lumen (as illustrated in FIG. 20). Alternatively, an over-the-wire type catheter can be used. The intermediate catheter 426 is delivered into the internal carotid artery 400 to a location just proximal to the occlusive device 422. Preferably, in order to maximize the effectiveness of the aspiration or irrigation, the catheter 426 is positioned less than two centimeters from the proximal end of the occlusive device 422 at some point during aspiration. Delivering the intermediate catheter 426 in such close proximity to the occlusion device 422 will allow the creation of a turbulent effect near the occlusive device during aspiration and irrigation thus aiding in the removal of the particles and debris. During aspiration, the intermediate catheter 426 can be moved in a proximal direction, to ensure more effective aspiration of the area.

Delivery of the intermediate catheter 426 near the occlusive device 422 requires passing the intermediate catheter 426 across the previously occluded vessel. In order to minimize the risk to the patient the intermediate catheter 426 is preferably soft, small and flexible. A preferred embodiment of this invention comprises delivering a soft-tipped intermediate catheter 426 made of a compound of a durometer 55 or less.

Once the intermediate catheter 426 is delivered in close proximity to the occlusive device 422, the area is first aspirated. As noted above, the intermediate catheter 426 can be moved backward in a proximal direction during aspiration. This forward and backward movement of the intermediate catheter 426 can be repeated as often as desired to provide effective aspiration. At some point during aspiration, the distal end of the aspiration catheter should be positioned about 2 cm or less from the proximal end of the occlusive device to ensure effective aspiration. Following aspiration, the area is irrigated by supplying a fluid, such as saline, through the intermediate catheter 426. The irrigation fluid acts to flush any remaining particles or debris from the internal carotid 400, to the external carotid 402, as indicated by the arrows in FIG. 21. The steps of sequential aspiration and irrigation or flushing, can be repeated as many times as necessary to remove all of the particles and debris from the vessel.

In one embodiment, the intermediate catheter 426 has a single lumen for delivery of aspiration pressure and irrigation fluid, such as the aspiration or irrigation catheters shown in FIGS. 7 through 16. The proximal end of the intermediate catheter 426 is connected to a source of negative pressure (as described above) and is used to aspirate the debris and particles around the occlusive device 422.

Following aspiration of the area, the proximal end of the intermediate catheter 426 is connected to a source of irrigation fluid, such as saline, in order to irrigate the area near the occlusive device 422. Preferably, the volume of fluid used to irrigate the area near the occlusive device 422 is equal to or greater than the volume of the area between the proximal end of the distal occlusive device and the start of the internal carotid artery at the bifurcation of the common carotid artery. For example, at least 10 cubic centimeters of fluid is delivered to the area that is between the distal occlusive device and the start of the internal carotid branch, which is approximately 1–5 cubic centimeters. As a result of this irrigation, any particles or debris remaining in the internal carotid 400 will be flushed into the external carotid 402.

In yet another embodiment, the intermediate catheter 426 has two lumens, one for aspiration and another for irrigation. The lumen providing aspiration is attached at its proximal end to a negative pressure source. A second lumen is attached at its proximal end to source of irrigation fluid. An advantage of this embodiment is that the particles and debris removed are in a separate lumen, eliminating the possibility that they could be flushed back into the vessel when the irrigation fluid is delivered through the same lumen as the aspiration pressure. As with the single lumen embodiment, the steps of aspirating and irrigating can be repeated as many times as necessary. Once the emboli have been flushed away, the distal occlusive device may be deactivated and removed from the patient.

Figure 22:
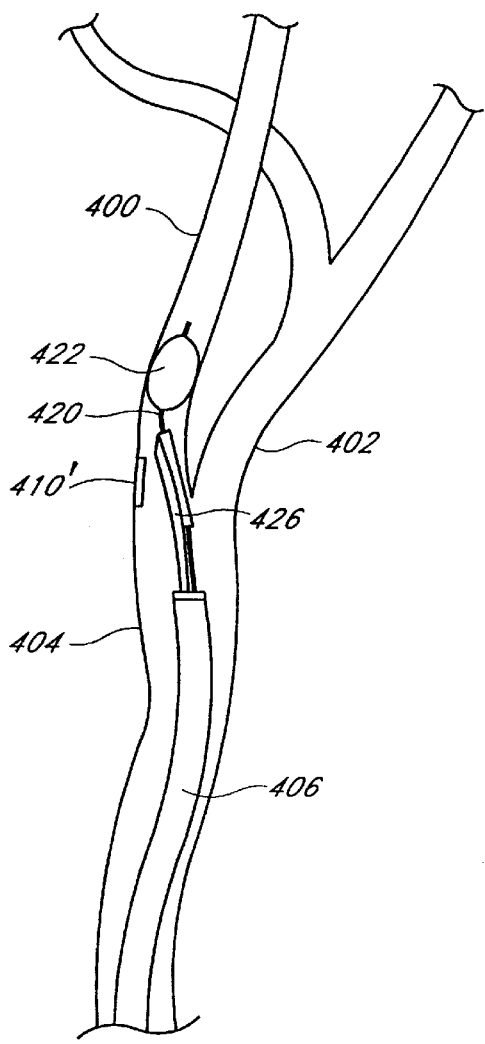
FIG. 22 is a perspective view showing a preferred location for the intermediate catheter when the intermediate catheter is used to flush away emboli from the treated occlusion.

As illustrated in FIG. 22, after the occlusion 410 has been treated, the distal end of the intermediate catheter 426 may be advantageously placed distal to the treated occlusion, i.e., between the treated occlusion 410' and the occlusive device 422. This facilitates more thorough flushing of the region between the occlusive device 422 and the treated occlusion 410', and around the treated occlusion generally, so that any particles and debris remaining after therapy can be more effectively removed as the aspiration fluid (i.e., blood from the common carotid) passes across the treated occlusion 410'.

Figure 23:
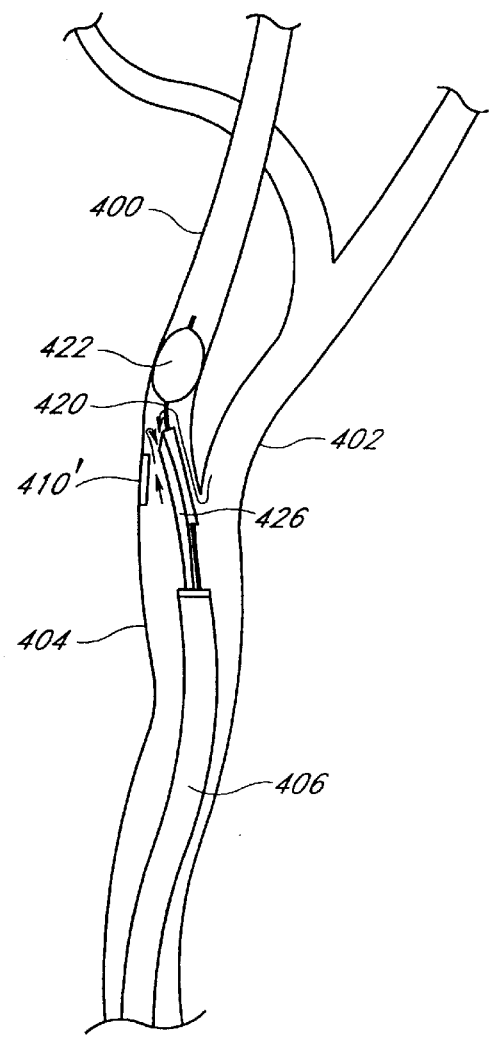
FIG. 23 is a perspective view of an embodiment in which the intermediate catheter is used for aspiration of emboli.

Flushing of the region in and around the treated occlusion 410' may be accomplished in a number of ways. For example, as illustrated in FIG. 23, the intermediate catheter 426 may be used as an aspiration catheter. Alternatively, as illustrated in FIG. 24, the intermediate catheter 426 may be used as an irrigation catheter, in which particles and debris are flushed towards the point where the common carotid 404 intersects the internal carotid 400, and towards the external carotid 402. Upon reaching the external carotid 402, particles, debris, and emboli are flushed down the external carotid with anatomical blood flow. The therapy catheter 448 of FIG. 24A may also be used for irrigation following therapy, in which saline solution is pumped through the annulus between the therapy catheter 448 and the guide-wire 420. The therapy catheter 448 advantageously comprises a therapy device (such as a balloon for balloon angioplasty, a stent, an atherectomy device for cutting away plaque, or a rheolitic catheter) for use after the occlusive device 422 is deployed.

The steps illustrated by FIGS. 23 and 24 may be performed sequentially, i.e., the intermediate catheter 426 may first be used as an aspiration catheter and then as an irrigation catheter. In FIGS. 23 and 24 (or 24A), the distal end of the catheter 426 (or therapy catheter 448) is preferably positioned beyond the treated occlusion 410' to more efficiently remove emboli from the treated region. In general, aspiration is performed as close to the occlusive device 422 as possible. The intermediate catheter 426 (like the therapy catheter 448) is advantageously separate from the guidewire 420 and slidable on it, so that the catheter 426 may be properly positioned by the user.

Figure 25:
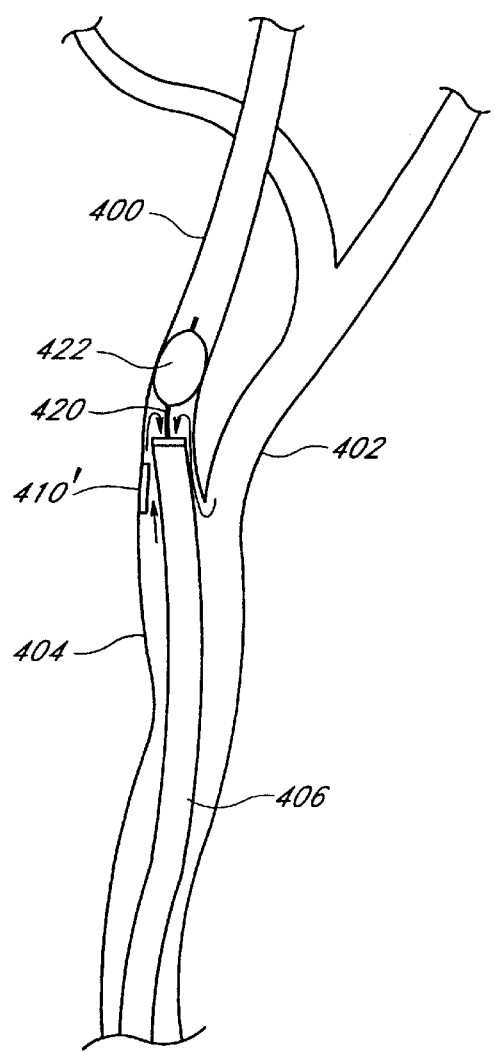
FIG. 25 is a perspective view of an embodiment in which the main catheter is used for aspiration of emboli.
Figure 26:
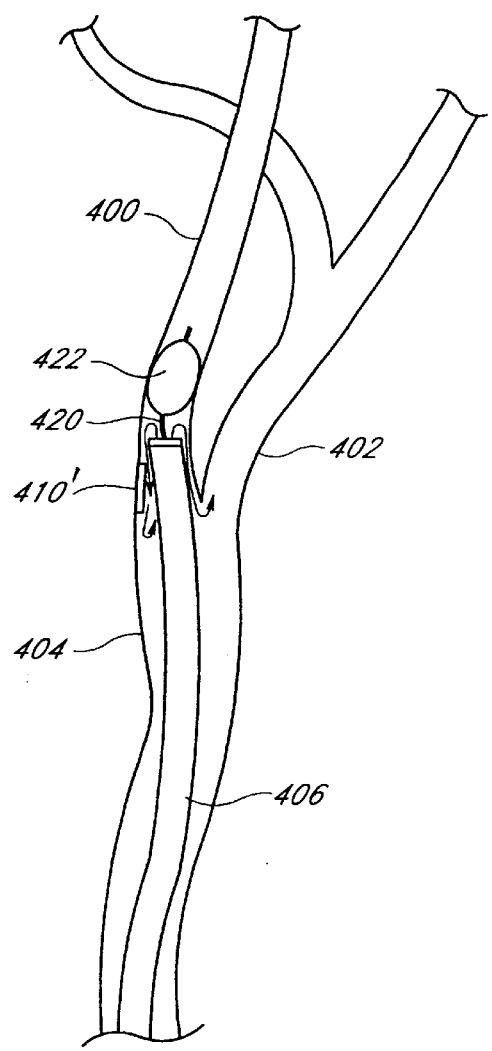
FIG. 26 is a perspective view of an embodiment in which the main catheter is used for irrigation of emboli.

The main (outer) catheter 406 itself may be used for aspiration and irrigation of the region in and around the treated occlusion 410', as illustrated in FIGS. 25 and 26, respectively. The main catheter 406 has a radial extent that permits the therapy catheter 448 and the intermediate catheter 426 to pass through the main catheter 406. In FIG. 25, the distal end of the main catheter 406 is positioned distal to the treated occlusion 410', and blood containing emboli or other particles is aspirated away into the main catheter and removed from the patient. In FIG. 26, the main catheter 406 is used to flush the region in and around the treated occlusion 410' by ejecting, for example, saline solution which then transports particles and debris away from the internal carotid

400 and down the external carotid 402. Either of the treatment methods illustrated by FIGS. 25 and 26 may be used to flush away particles, or both may be used sequentially, e.g., the main catheter 406 may be used for aspiration and then for flushing. (However, the presently preferred methods utilize the main catheter 406 only for irrigation.)

Other combinations of the methods illustrated by FIGS. 23–26 can be utilized. For example, the intermediate catheter 426 of FIG. 23 may be used for aspiration, followed by flushing with the main catheter 406 (as illustrated in FIG. 26). Also, the main catheter 406 may be used for aspiration (as illustrated in FIG. 25), followed by flushing with the intermediate catheter 426 (as illustrated in FIG. 24). In general, the best results are obtained by first aspirating (thereby removing particles from the patient) and then flushing, and the aspirating and flushing steps may be repeated as necessary. The same catheter can be used for aspiration and then irrigation, but in this case, this catheter should be removed from the patient and cleaned after aspiration to remove emboli from it. Irrigation then removes any emboli remaining in the patient. (However, if the main catheter 406 is used for both aspiration and irrigation, this cleaning step should be foregone since the main catheter 406 should be the last catheter to be removed from the patient.) It is preferred, however, to use a separate aspiration catheter and irrigate through the main catheter 406.

Aspiration and irrigation may be performed simultaneously by having two catheters deployed at the same time and irrigating through one (e.g., the therapy catheter 448 or the intermediate catheter 426) and aspirating through another (e.g., the main catheter 406). In this case, the main catheter 406 may be deployed to a location near the intersection of the internal carotid 400 and the external carotid 402. Alternatively, aspiration may be performed through the intermediate catheter 426 while irrigating through the main catheter 406, in which the distal ends of the intermediate catheter 426 and the main catheter 406 are preferably positioned distal and proximal, respectively, to the treated lesion 410'.

Figure 27:
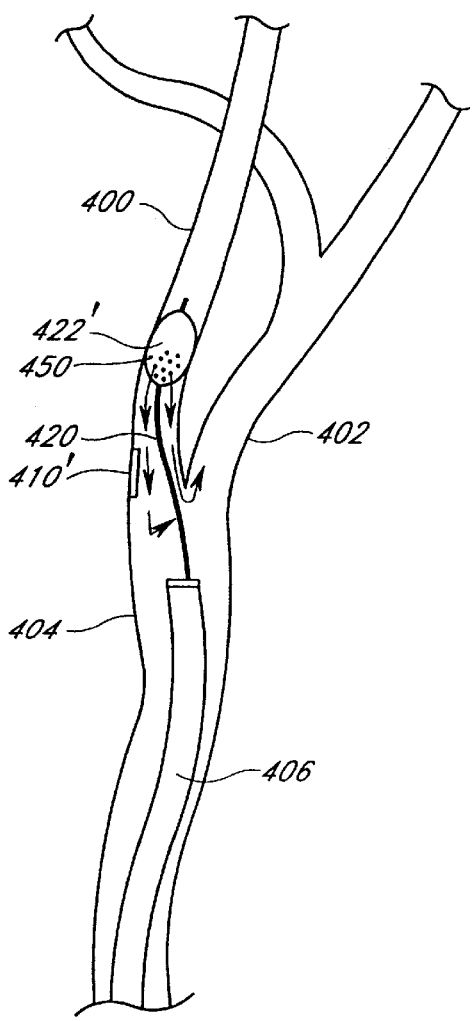
FIG. 27 is a perspective view of an embodiment in which a distal occlusion device has a plurality of holes therein for passing irrigation fluid across the treated occlusion.

As shown in FIG. 27, flushing may also be performed in a blood vessel (not necessarily a bifurcated vessel as illustrated herein), using an occlusive device 422' that passes saline solution (or another suitable flushing solution). In this embodiment, the saline solution may be advantageously passed through a lumen in the guidewire 420 and into the occlusive device 422'. The occlusive device 422' has at least one fluid flow opening and is preferably microporous on its proximal end, having a plurality of holes 450 (e.g., 10–50) that are preferably less than 1000 microns in diameter and more preferably between 50 and 100 microns in diameter. The holes may be formed in the occlusive device 422' by laser drilling, for example. As saline solution passes through the occlusive device 422' and into the internal carotid 400, emboli, particulates, and other debris are flushed past the treated occlusion 410' and down the external carotid 402. During irrigation, the fluid flow may be maintained with a pressurized syringe located outside the patient. However, while therapy is being performed on the occlusion 410, the fluid flow may be advantageously reduced to avoid overpressurizing that segment of the internal carotid artery 400 between the occlusion device 422' and the occlusion 410 (pressures should be kept less than 50 psi). Thus, the saline solution is used for inflating the occlusive device 422' as well as for irrigating emboli from the internal carotid 400 down the external carotid 402. The irrigation method of FIG. 27 may be augmented by aspirating the region in and around the treated occlusion 410' through a catheter, e.g., through the intermediate catheter 426 (as in FIG. 23) or the main catheter 406 (as in FIG. 25).

Figure 28:
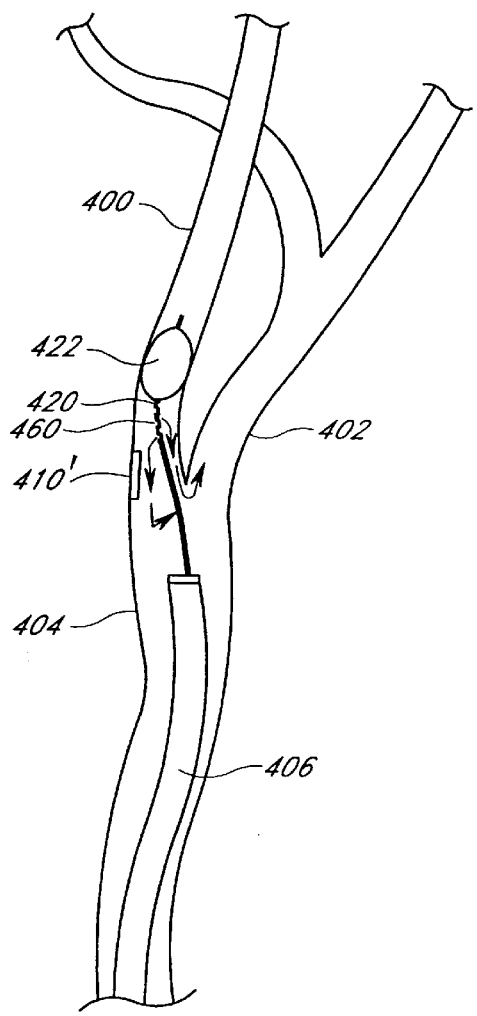
FIG. 28 is a perspective view of an embodiment in which an elongate member (e.g., a guidewire) has a plurality of holes therein for passing irrigation fluid across the treated occlusion.

Another irrigation device and method is disclosed in FIG. 28, in which one or more holes 460 in the guidewire 420 are located distal to the treated lesion 410' and proximal to the occlusive device 422. (For example, 1, 2, or 3 holes of dimensions 0.050"×0.002–0.003" maybe used, or 10 holes of dimensions 0.003"×0.003", to provide a flow such that the pressure inside the vessel does not exceed 50 psi.) Irrigation fluid is pumped through the guidewire 420 and out of the holes 460 (which may advantageously be 50–300 microns in diameter) to flush away emboli from the treated lesion 410' and down the external carotid 402. The guidewire 420 may have a single lumen (not shown) that is in fluid communication with both the internal carotid artery 400 (via the holes 460) and the occlusive device 422, in which case the irrigation fluid and the fluid used to inflate the occlusive device 422 are the same. Alternatively, the guidewire 420 may have dedicated lumens (not shown) for irrigation and inflation. The irrigation method of FIG. 28 may be augmented by aspirating the region in and around the treated occlusion 410' through a catheter, e.g., through the intermediate catheter 426 (as in FIG. 23) or the main catheter 406 (as in FIG. 25).

Instead of pumping irrigation fluid through the holes 460 as shown in FIG. 28, a larger slot (not shown) of dimensions 0.005"×0.100–0.200" may be cut into the guidewire 420 and then covered with a braid (not shown) that extends 0.010–0.030" beyond the edges of the slot. As irrigation fluid is passed through the guidewire 420, the braid expands, permitting the irrigation fluid to pass out of the slot and into the internal carotid 400. Instead of using a braid, this slot may alternatively be covered with a plastic sheath (not shown) having a plurality of slits or pores (not shown) which are in fluid communication with the slot. Ten pores having a diameter of 50–100 microns may advantageously be used.

Irrigation rates for the methods disclosed herein are preferably between 0.1 cc/sec and 3 cc/sec, more preferably between 0.5 and 1.5 cc/sec, and still more preferably about 1 cc/sec. Aspiration rates are preferably between 0.5 and 5 cc/sec, and more preferably between 0.5 and 1.1 cc/sec. The fluid pressure used to generate the irrigation and aspiration rates may be pulsed on and off to better flush away emboli. For example, fluid pressure may be alternately applied for 5 seconds (in the form a pulse) and then turned off for 2–3 seconds. In general, fluid is irrigated (or aspirated) through a lumen in a catheter, with the lumen being in fluid communication with a fluid flow opening at a distal end portion of the catheter.

The single balloon methods disclosed herein may additionally comprise inflating a balloon on the main catheter 406 within the common portion of the vessel to occlude the common portion.

D. Alternate Dual Balloon System

Figure 21:
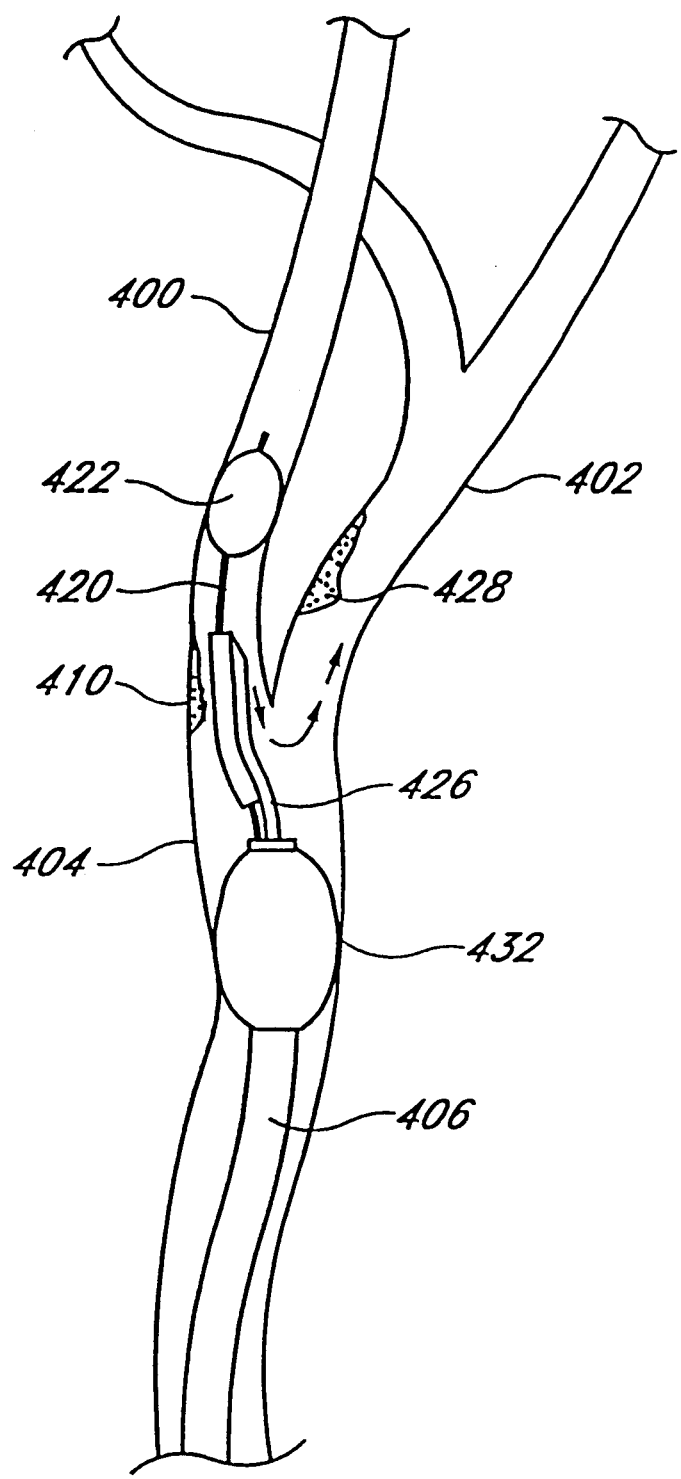
FIG. 21 is a perspective view of still another example of an emboli containment and removal method which employs two occlusive devices.

Under certain circumstances, use of a second occlusive device is desired, as illustrated in FIG. 21. The second occlusive device 432 is positioned on the distal end of the main catheter 406 and acts to occlude the main carotid artery 404. A second occlusive device 432 may be desired where the physician is concerned about crossing the occlusion 410 in the internal carotid artery 400 with the inner catheter 420 or where there is another occlusion 428 in the external carotid artery 402 resulting in decreased flow through the external carotid 402.

Once the main catheter 406 is delivered to the common carotid artery 404, the occlusive device 432 is activated. The activation of the occlusive device 432 will have the effect of occluding the common carotid artery 404 thereby cutting off the blood flow to both the internal carotid 400 and the external carotid 402 arteries.

Next, an inner catheter 420 with an occlusive device 422 is delivered distal to the occlusion 410 in the internal carotid artery 400 and activated, thus isolating the occlusion 410 between the two occlusive devices 432, 422. This is followed by therapy on the occlusion 410 as described above. Sequential aspiration and irrigation are then performed as described above.

The main advantage of using two occlusive devices is that when the internal carotid artery 400 is irrigated, a back pressure is created in the chamber defined by the proximal occlusive device 432 and the distal occlusive device 422. This back pressure will force the fluid, particles and debris from the internal 400 and common 404 carotid arteries through the external carotid artery 402.

E. Alternate Triple Balloon System

In some cases, a triple balloon system is used. This system is especially advantageous in those patients where occlusion of the common carotid artery results in blood from collateral vessels flowing from the external carotid artery to the internal carotid artery. The direction of blood flow in a particular patient can be determined through angiography.

In this system (not shown), following activation of the occlusive device in the common carotid artery, but before crossing the occlusion with an inner catheter, a first inner catheter with an occlusive device is delivered to the external carotid artery and the occlusive device activated. This prevents flow from collateral blood vessels moving from the external to the internal carotid artery. Next, a second inner catheter is delivered to the internal carotid artery past the site of the occlusion and the occlusive device activated to occlude the internal carotid artery. Alternatively, the first inner catheter can be positioned within the internal carotid artery and the occlusive device activated, followed by delivery of the second inner catheter to the external carotid artery and activation of the occlusive device. In either case, the occlusion is completely isolated between the three occlusive devices. This is followed by therapy on the occlusion, aspiration, and irrigation if desired, as described above.

F. Use of Occlusive Devices in Combination with Perfusion

Figure 29A:
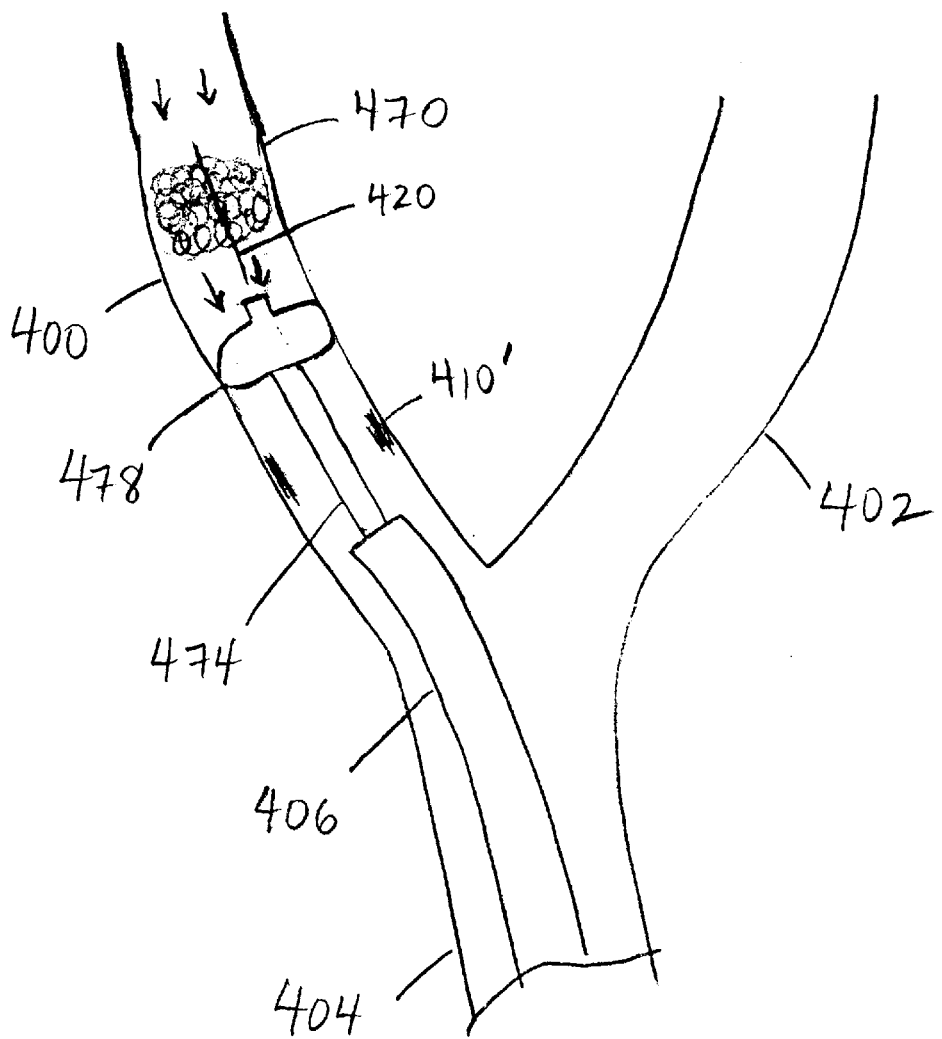
FIGS. 29A and 29B are perspective views of an embodiment in which a perfusion-filter located distal to the lesion to be treated permits the perfusion of blood while entraining emboli produced as a result of therapy.
Figure 29B:
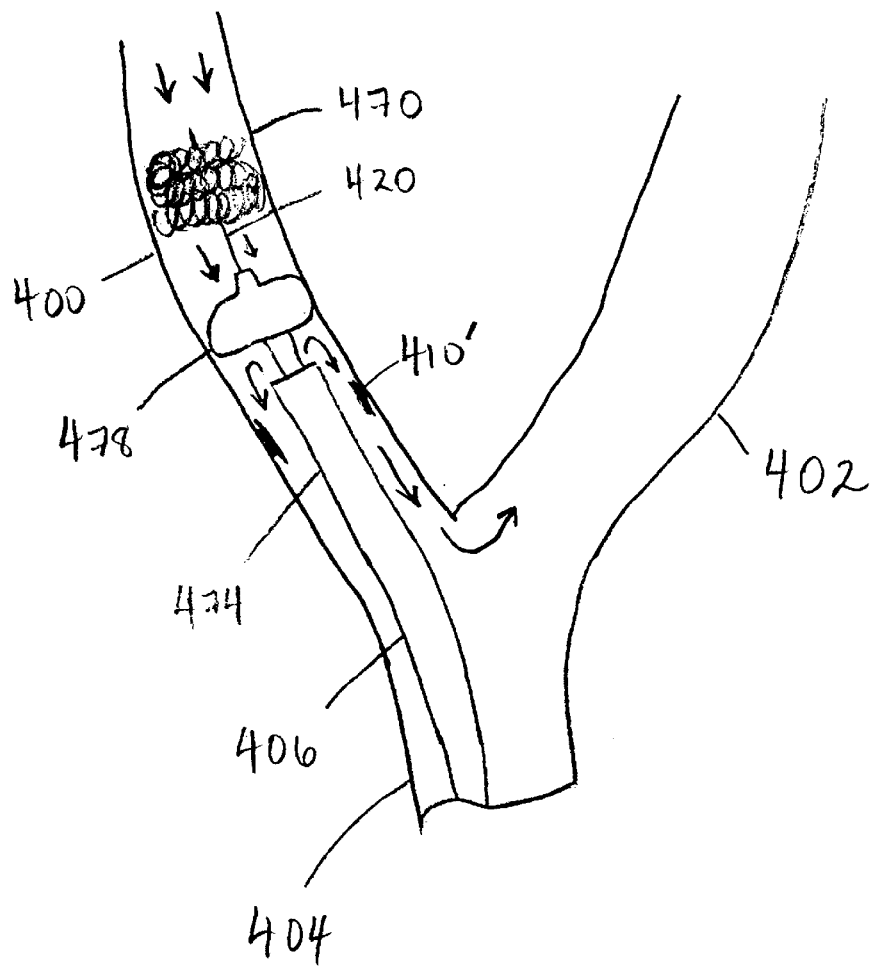

For some applications, it may be desirable to provide for the perfusion of blood while medical procedures are performed on a blood vessel such as the internal carotid artery. Several such embodiments are now discussed in connection with FIGS. 29-32. Perfusion may be necessary for those patients who can not tolerate an excessive reduction of blood flow to their brain. One exemplary method is illustrated in FIGS. 29A and 29B. FIG. 29A shows a guidewire 420 to which an expandable member 470 is attached. In its undeployed state, the expandable member 470 has a relatively narrow profile so that the member 470 may be delivered through a blood vessel. The expandable member 470 may be, for example, a mesh- or filter-like device which, when deployed, permits the perfusion of blood but is capable of entraining emboli. After positioning the (undeployed) expandable member 470 distal to the lesion 410 within the internal carotid artery 400 to be treated, the member 470 may be deployed so that it expands to fill the internal carotid artery. The expandable member 470 may be deployed by any one of a number of techniques, for example, the distal end of the member 470 may be attached to a pull wire (not shown) that passes through the guidewire 420 such that when the pull wire is retracted, the member 470 expands to fill the internal carotid artery 400. (Conversely, in this example, the member 470 may be returned to its undeployed position when the pull wire moves in the distal direction.) Alternatively, the member 470 may be self-expanding and deployed by retracting a low profile sheath (not shown) that surrounds the expandable member.

After the expandable member 470 is deployed, therapy may be performed on the lesion 410, resulting in a treated lesion 410'. To this end, a therapy catheter (not shown in FIGS. 29A and 29B) may be deployed over the guidewire 420, and any one of a number of therapy operations performed, such as balloon angioplasty, deploying a stent, or the application of drug therapy. The therapy catheter may then be withdrawn from the patient. Emboli that are created as a result of the therapy are blocked by the expandable member 470 when these emboli are flushed distally by anatomical blood flow, so that the emboli are prevented from traveling downstream towards the brain, for example. However, the expandable member 470 still permits the perfusion of blood, so that the health of tissue supported by the internal carotid artery 400 is not jeopardized.

Following removal of the therapy catheter, an intermediate catheter 474, to which an occlusive device 478 (such as an occlusion balloon) is attached, is directed through the common carotid 404 (by passing the catheter 474 over the guidewire 420 and through a guide or main catheter 406) and positioned such that the occlusive device 478 is distal to the treated lesion 410' and proximal to (and preferably adjacent proximal to) the expandable member 470. The occlusive device 478 may then be deployed to occlude the internal carotid artery 400, thereby preventing anatomical blood flow. Emboli that have been entrained within the expandable member 470 may then be advantageously aspirated away by applying suction through the intermediate catheter 474, such that blood distal to the expandable member 470 passes through the expandable member, entraining emboli in the process. The aspirated emboli and blood pass through the intermediate catheter 474 and are directed out of the patient. If the expandable member 470 is clogged, aspiration will nevertheless draw emboli from the expandable member by drawing blood from the proximal side of the expandable member.

To remove any emboli that may be remaining in and around the treated lesion 410', the main catheter 406 may be brought distal to the treated lesion, as illustrated in FIG. 29B. With the occlusive device 478 still deployed, irrigation fluid is ejected from an opening near the distal end of the main catheter 406, such that emboli are carried towards the intersection of the internal carotid 400 and the external carotid 402, whereupon the emboli are flushed down the external carotid 402 by anatomical blood flow. The expandable member 470 may be retracted, preferably while aspirating through the intermediate catheter 474, so that any emboli that are dislodged during the retraction of the expandable member are removed from the patient. The expandable member 470, the intermediate catheter 474, and the main catheter 404 may then be removed from the patient.

Figure 30A:
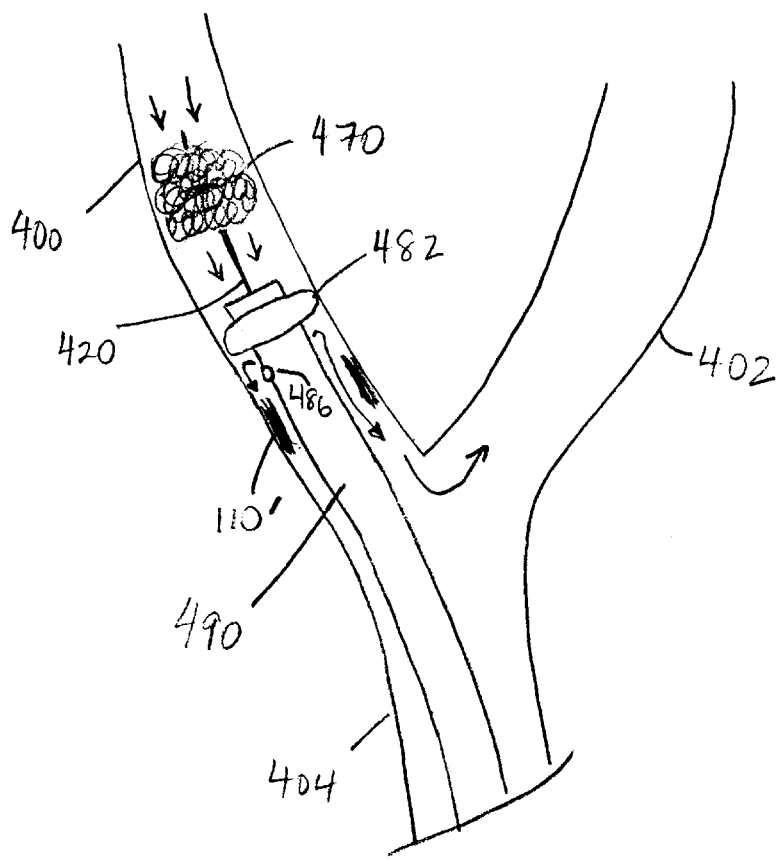
FIG. 30A is a perspective view of an alternative embodiment in which emboli are captured in a perfusion-filter.
Figure 30B:
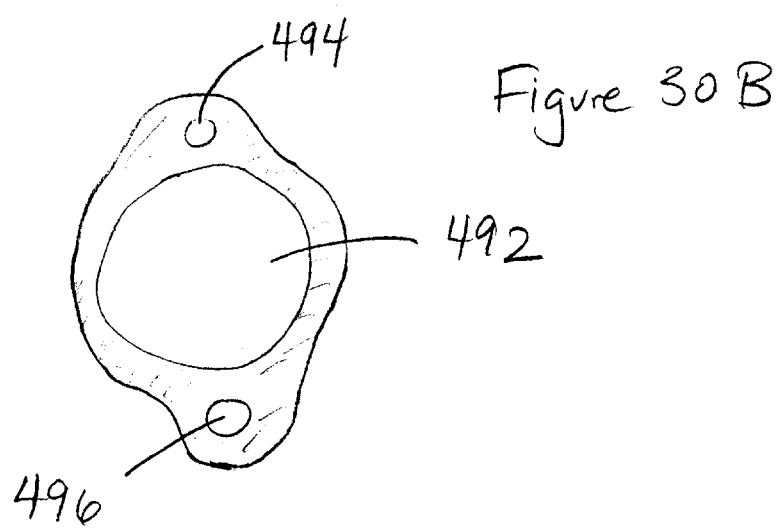
FIG. 30B is a cross sectional view of the main catheter of the embodiment of FIG. 30A, illustrating lumens used for inflation of the occlusive device, for delivering irrigation fluid, and for passing an elongate member (e.g., a guidewire).

Another embodiment in which an occlusive device is combined with perfusion is illustrated in FIGS. 30A and 30B, in which the expandable member 470 is positioned and deployed distal to the lesion 410 as in the embodiment of FIG. 29A. After performing therapy on the lesion 410, a catheter such as an outer catheter or main catheter 490 is brought distal to the treated lesion 410'. An occlusive device 482, such as a balloon, located on the main catheter is then deployed, occluding the vessel 400. Aspiration is then performed through the main catheter 490, so that blood flows through the expandable member 470 and into the main catheter, thereby removing emboli trapped in the expandable member, which may have been produced as a result of therapy. If the expandable member 470 is clogged, aspiration will nevertheless draw emboli from the expandable member by drawing blood from the proximal side of the expandable member. Irrigation fluid may be advantageously ejected from one or more openings 486 in the main catheter 490 distal to the treated lesion 410', so that emboli remaining in and around the treated lesion are flushed towards the intersection of the internal carotid 400 and the external carotid 402, whereupon they are flushed down the external carotid by anatomical blood flow. The aspiration and irrigation steps may be performed sequentially or simultaneously. While the expandable member 470 is retracted, aspiration is preferably performed to remove any emboli that are dislodged during the process of retracting the member 470.

FIG. 30B shows the cross section of the main catheter 490, illustrating that the main catheter 490 of FIG. 30A has at least three lumens—a lumen 492 for passing the guidewire 420 and the therapy catheter (not shown in FIG. 30A), a lumen 494 for inflating the occlusive device 482, and a lumen 496 for delivering irrigation fluid to one or more openings 486 distal of the treated lesion 410'.

Figure 31:
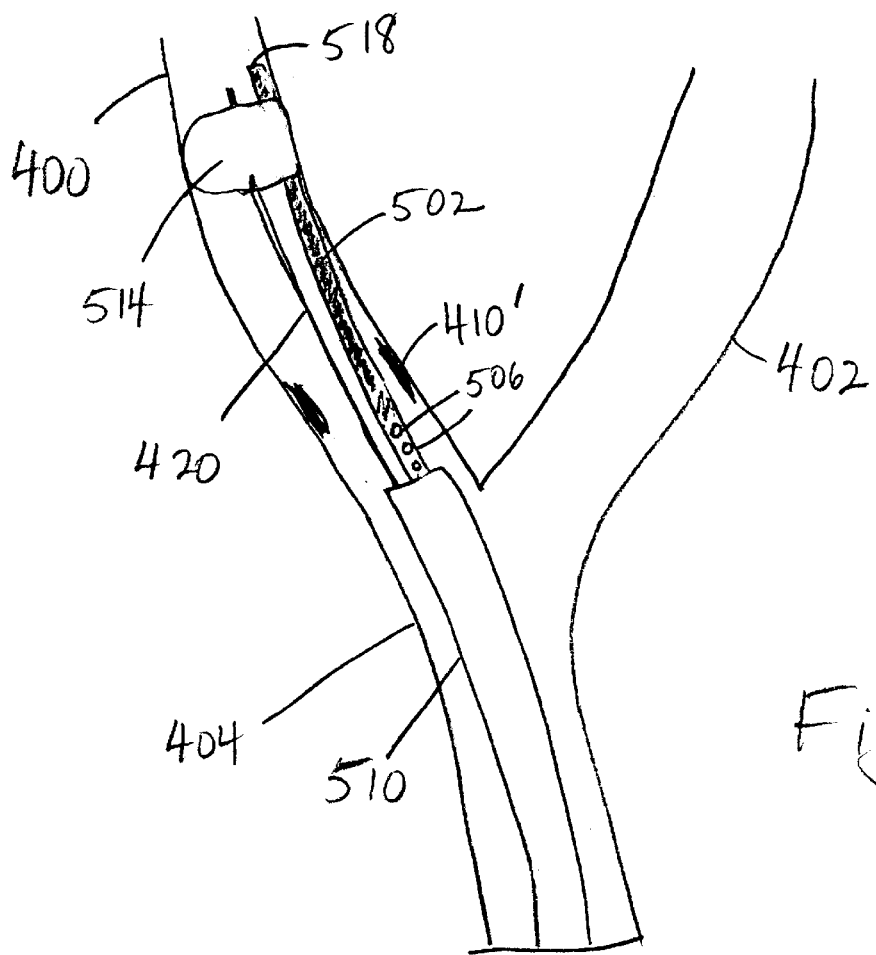
FIG. 31 is a perspective view of an embodiment in which passive perfusion is performed with a hypotube having holes therein.

Yet another embodiment in which an occlusive device is combined with perfusion is illustrated in FIG. 31, in which a hypotube 502 having a plurality of holes 506 is passed through an outer or main catheter 510. In the embodiment illustrated in FIG. 31, an occlusive device such as an occlusion balloon 514 is used rather than the expandable member 470, and the hypotube 502 extends beyond the occlusion balloon 514 in the distal direction to provide perfusion while therapy is performed on a lesion 410.

After positioning the (uninflated) occlusion balloon 514 distal of the lesion 410 and positioning an opening 518 of the hypotube 502 distal of the occlusion balloon 514, the occlusion balloon is inflated so that the occlusion balloon occludes the vessel 400 while contacting the hypotube 502. (The holes 506 in the hypotube 502 are preferably located at least 1–2 mm proximal of the lesion to reduce the risk of emboli entering the holes and traveling distal of the occlusion balloon 514.) Therapy is then performed on the lesion 410, while the inflated balloon 514 blocks emboli (produced as a result of the therapy) from traveling downstream. However, blood may still pass through the holes 506 in the hypotube 502 and exit the opening 518 in the hypotube, so that perfusion of blood is allowed. After the therapy is complete and the therapy catheter is removed, a fluid port of the catheter 510 may be advantageously positioned distal to the treated occlusion 410' (and proximal to the balloon 514) and irrigation fluid delivered distal to the treated lesion 410', so that fluid flows across the treated occlusion in a distal to proximal direction. The irrigation fluid carries away emboli towards the junction of the internal carotid 400 and the external carotid 402, whereupon the emboli are flushed down the external carotid by anatomical blood flow. As an alternative (not shown) to using a hypotube dedicated for perfusion, holes may be introduced into the guidewire, with the guidewire having a lumen that extends through the occlusion balloon leading to an opening distal of the balloon. The holes 506 in the hypotube 502 or in the guidewire 420 may advantageously have diameters of 0.005" or larger, or slits of dimensions 0.005"×0.005". Several such hole (or slits) are preferably used to create a flow of blood of between 8 and 50 cc/min.

The perfusion illustrated in FIG. 31 is passive, since the blood passes through the hypotube 502 on its own. In the case of active perfusion, a pump such as a syringe pump (not shown) may be attached to the proximal end of a hypotube that does not have holes. Alternatively, a guidewire such as guidewire 420 may be used in which the guidewire passes through the occlusive device 422—such a guidewire has a lumen therein having an opening which is distal to the balloon 514. The lumen could have a diameter between 0.010" and 0.025", and more preferably a diameter of about 0.018". A preferred pump rate is between 8 and 40 cc/min.

Figure 32A:
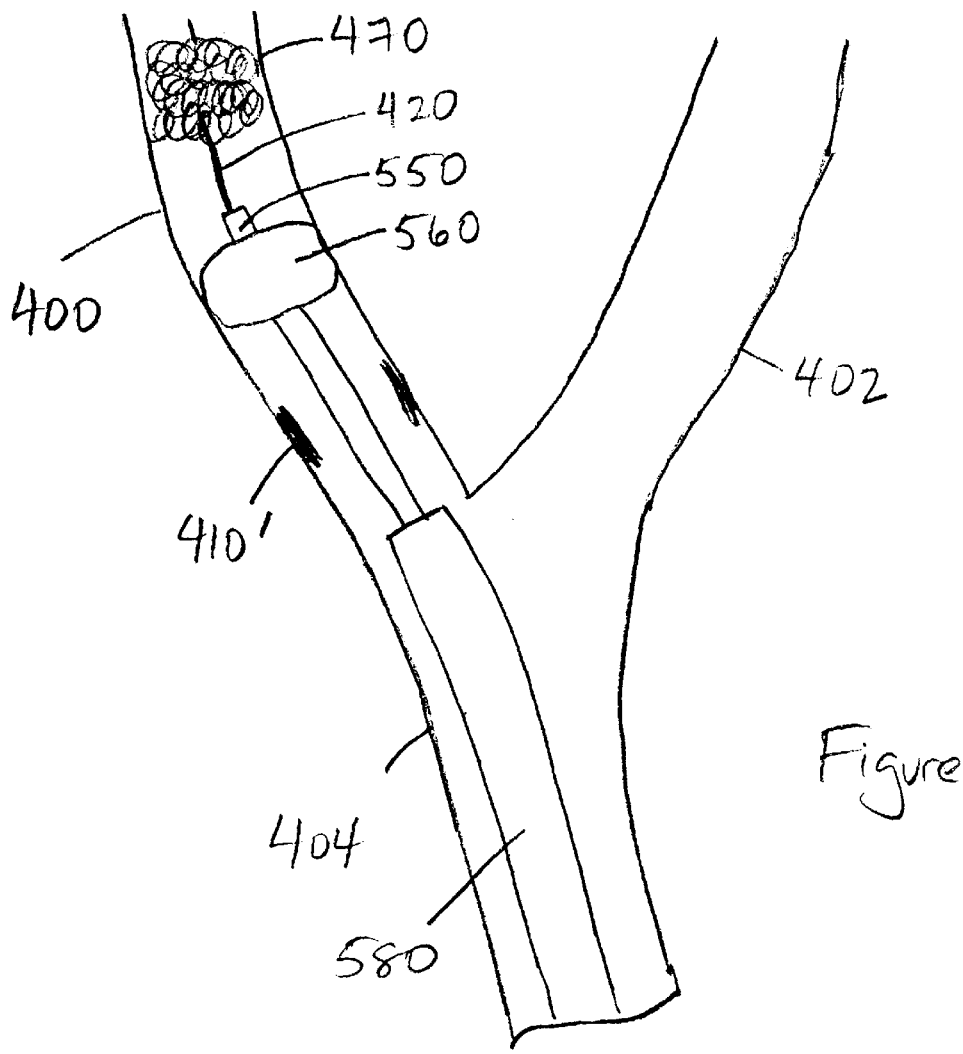
FIGS. 32A and 32B are perspective views of a perfusion-filter embodiment in which the occlusion of the vessel is performed with the therapy catheter.
Figure 32B:
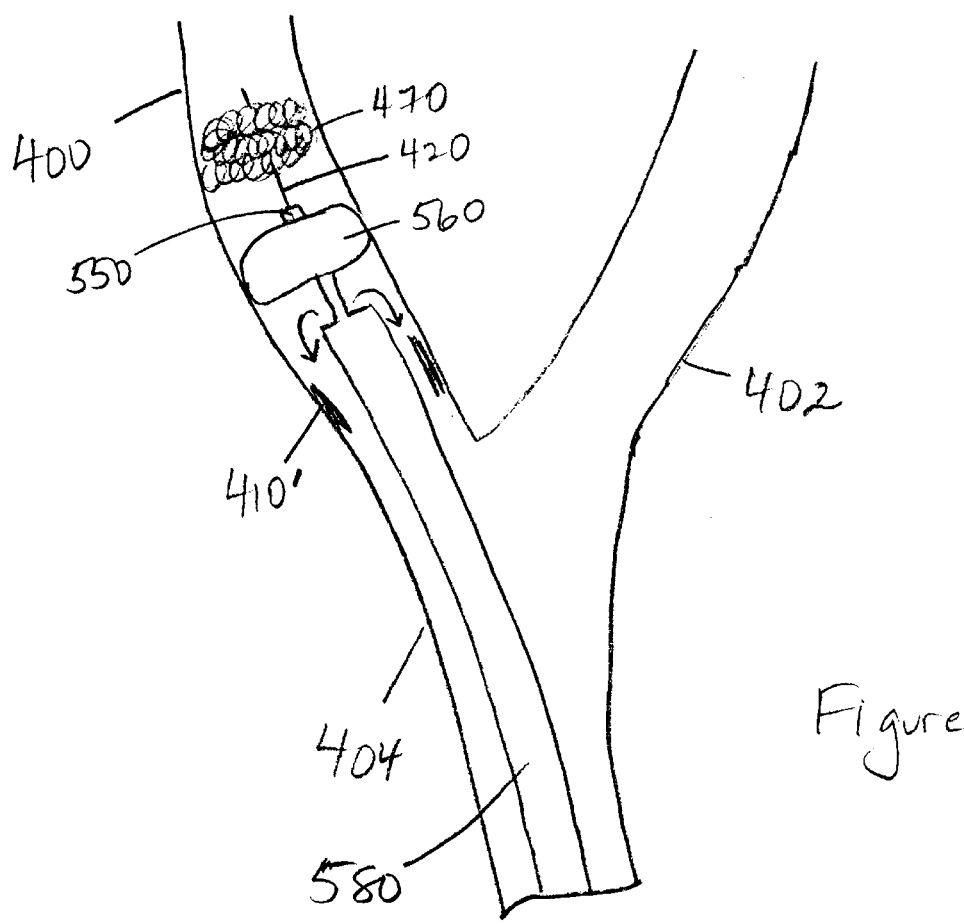

Another embodiment that combines features of occlusion with perfusion is illustrated in FIGS. 32A and 32B. The guidewire 420 is brought through the vessel 400 until the expandable member 470 is located distal to the lesion 410 to be treated. After deploying the expandable member 470, therapy is performed on the lesion 410, e.g., using a therapy catheter 550 to which an angioplasty balloon 560 is attached. During and after performing therapy on the lesion 410, the expandable member 470 collects emboli that may be produced as a result of the therapy, as blood travels from one side of the expandable member to the other in a proximal to distal direction. After performing therapy (e.g., after deploying the angioplasty balloon 560), the angioplasty balloon 560 is deflated and the therapy catheter 550 is moved over the guidewire 420 in the distal direction such that the angioplasty balloon 560 is distal of the treated lesion 410'. The angioplasty balloon 560 is then reinflated so that the vessel 400 is occluded. With the vessel 400 occluded, a catheter 580 such as an outer or main catheter is then positioned such that a fluid port of the catheter 580 is distal of the treated lesion 410'. As illustrated in FIG. 32B, irrigation fluid is ejected from the catheter 580 to flush away any emboli that may remain in and around the treated lesion 410'. The irrigation fluid and any emboli entrained within it travel in a distal to proximal direction towards the intersection of the internal carotid 400 and the external carotid 402, whereupon the irrigation fluid and emboli are carried down the external carotid artery 402 by anatomical blood flow. (Alternatively, the catheter 580 may be used to aspirate the region in and around the treated lesion 410' to create a flow of fluid in the proximal to distal direction.) The expandable member 470, the therapy catheter 550, and the catheter 580 can then be removed from the patient. When removing the expandable member 470 from the vessel 400, however, care should be taken to avoid introducing any emboli into the bloodstream.

G. Accommodating Changes in Vessel Diameter

As a result of therapy being performed on a lesion, the diameter of the vessel or vessels being occluded may increase. For example, if the internal carotid artery is occluded distal to a lesion within the carotid artery, and then treatment is performed on that lesion, the diameter of the internal carotid artery may increase substantially as a result of the treatment. If the occlusive device in the internal carotid does not accommodate this increase in diameter, resulting in a break in the seal between the occlusive device and the walls of the internal carotid, the risks to the patient may be significant.

A method for avoiding this possibility involves applying an expansion force to the occlusive device beyond that which is required to seal the occlusive device to the walls of the vessel. For example, if an occlusion balloon is used as the occlusive device in the internal carotid, then the balloon may be advantageously inflated to a pressure beyond that which is required to maintain a seal in the internal carotid. As the balloon begins to be inflated, it will expand both axially and radially. The balloon continues to expand radially until it mates with the walls of the vessel, at which point further expansion of the balloon in the radial direction is hindered by the tendency of the vessel to resist enlargement. Continuing to inflate the balloon at this point results in the balloon expanding preferentially in the axial direction, rather than in the radial direction. As the balloon expands in the axial direction, potential energy continues to be stored up in the balloon.

If the vessel expands (e.g., as a result of therapy being performed on it), then the potential energy stored in the balloon is harnessed in that the balloon expands in the radial direction (while correspondingly contracting somewhat in the axial direction), such that the balloon continues to make contact with the vessel during and following treatment, thereby preventing a break in the seal which could result in injury to the patient. Thus, with such a method, it is not necessary to actively adjust the pressure in the balloon as a result of treatment of a lesion, and in this sense, the seal is self-accommodating with respect to changes in vessel diameter.

The occlusive device may also comprise a self-expanding material such as nitinol, for which it is possible to obtain a nearly constant level of stress over a relatively wide range of strain. For example, if an occlusive device comprising a nitinol filter-like mesh is capable of sealing a 6 mm diameter vessel, such an occlusive device may be used to occlude a vessel that is initially 5 mm in diameter, so that if the vessel expands, the perfusion-filter will also expand to maintain occlusion within the vessel.

The diameter of the internal carotid artery may increase substantially as a result of therapy performed on it. For example, a vessel that has a 4 mm diameter at the point where the occlusion balloon is located may increase to 5 mm or more as a result of therapy. Thus, in this method, the balloon may be advantageously positioned in a blood vessel such that the vessel diameter is at least 20% less than the maximum useful sealing diameter of the balloon. As the lesion is treated, the balloon will continue to seal against the walls of the vessel, even if the diameter of the vessel should expand in response to the treatment. This method can be used with a variety of expandable members other than balloons, such as braids, coils, ribs, ribbon-like structures, slotted tubes, and filter-like meshes, which may be partially or completely covered with a membrane or another covering to provide a seal with the vessel.

H. Inflation Apparatus

Figure 33:
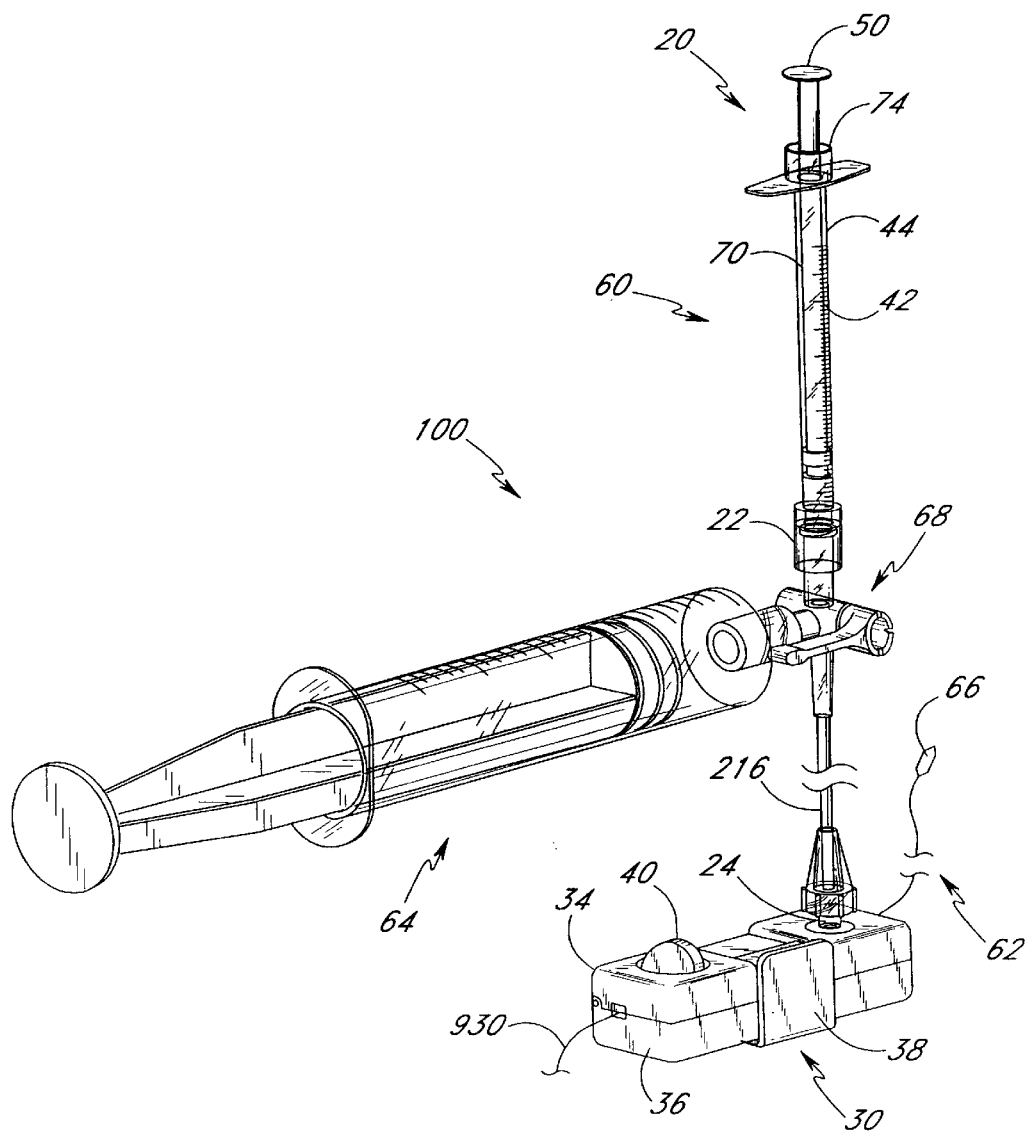
FIG. 33 shows a preferred embodiment of a syringe assembly having features in accordance with the present invention and operably coupled to an illustrative inflation adapter at a proximal portion of a balloon guidewire catheter.

A preferred embodiment of a low volume or inflation syringe 60 in a syringe assembly 100 for inflating an occlusion balloon in accordance with the present invention is shown in FIG. 33. Also shown in FIG. 33 is an illustrative connection of the assembly 100 to an occlusion balloon guidewire catheter 62 (such as guidewire 420) utilizing an inflation adapter 30. The syringe assembly 100, comprising the inflation syringe 60 and a larger capacity or reservoir syringe 64, is attached via tubing 216 to the inflation adapter 30 within which a sealing member 930 (see FIGS. 34A and 34B) and the balloon catheter 62 are engaged during use. Alternatively, other devices that control the flow of inflation fluid, such as flow controllers, may be used.

Figure 34A:
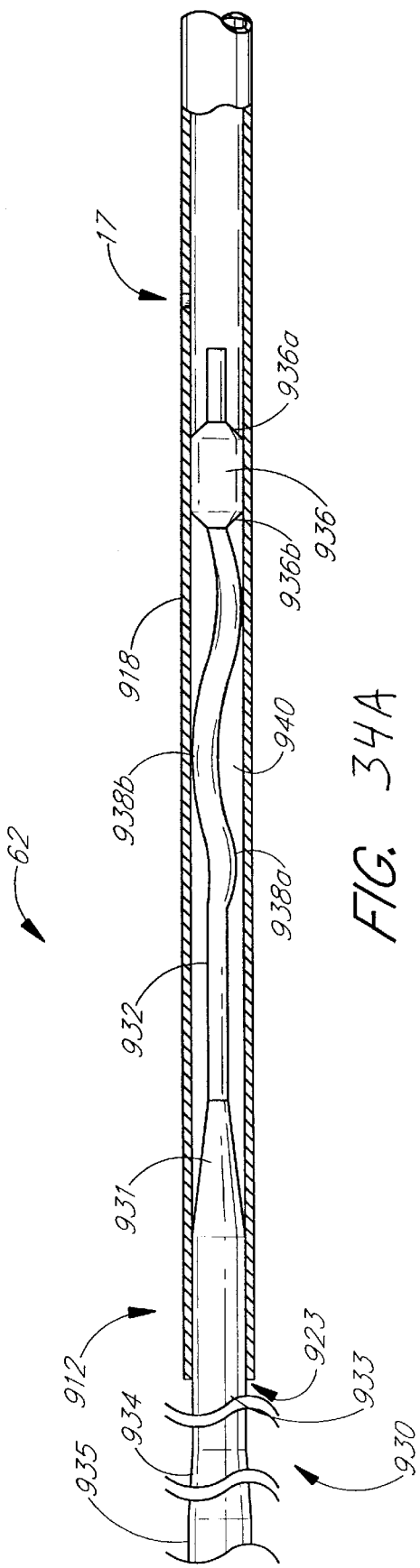
FIGS. 34A and 34B show open and closed positions, respectively, of the sealing member, which is used with the balloon guidewire catheter of FIGS. 33 and 35.
Figure 34B:
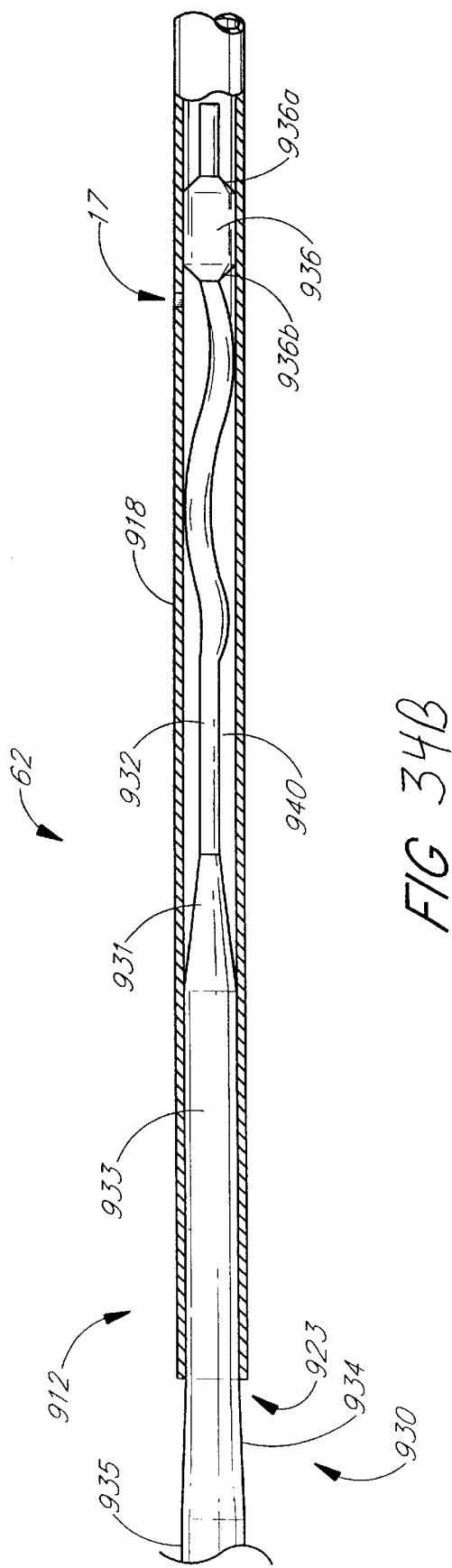
Figure 35:
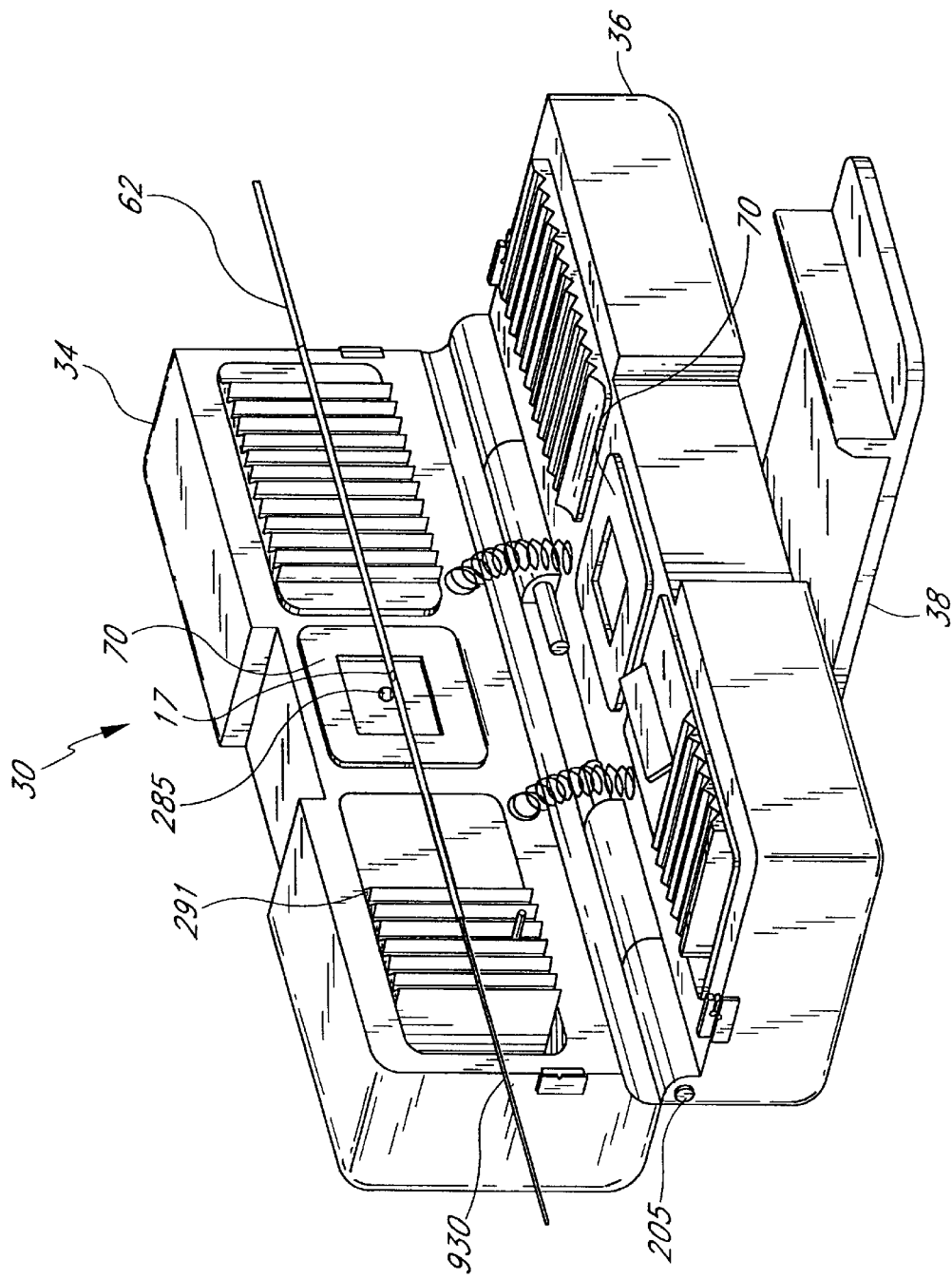
FIG. 35 shows a perspective view of the balloon guidewire catheter of FIG. 33 placed within an open inflation adapter.

The sealing member 930, described in more detail below in connection with FIGS. 34A and 34B, is inserted into an open proximal end of the catheter 62. The syringe 60 is used to inject inflation fluid through the adapter 30 and inflation port 17 into a lumen of the catheter 62, and into a balloon 66 (such as balloon 422). The inflation adapter 30, described in more detail below in connection with FIG. 35, is used to open and close the sealing member 930 to permit the inflation or deflation of the balloon 66 mounted on the distal end of the catheter 62. However, it will be emphasized that other types of adapters, valves, and/or sealing members can be employed with the inflation syringe and/or syringe assembly of the present inflation, in order to achieve rapid and accurate inflation/deflation of medical balloons or other nonballoon medical devices. Therefore, although illustrated in connection with a low volume occlusion balloon 66, other types of balloons and nonballoon devices may be utilized.

If the balloon 66 is mounted on the distal end of the catheter 62, the syringe 60 and/or syringe assembly 100 is preferably connected at the proximal end of the catheter 62. Prior to use of the syringe 60 to inflate the balloon 66 to the proper size for the vascular segment to be treated, the distal end of the catheter 62 and the balloon 66 are first "primed" or evacuated. The reservoir syringe 64 of the assembly 100 may be used for the evacuation. Access to the vascular site is through a port in the patient obtained, for example, using an introducer (not shown). A preferred system and method for accomplishing the occlusion balloon inflation is described below.

The inflation syringe 60 may be provided with a stop mechanism 20 for limiting both the intake of fluid into the syringe and the delivery of fluid from the syringe. The syringe 60 has an elongate cylinder 44 and plunger arrangement 50 which provide for greater displacement or travel by the plunger along the cylinder length than is necessary to expel a relatively small amount of inflation fluid. Thus, with the stop mechanism 20, the clinician is provided with an enhanced sense of whether the fluid in the syringe 60 has been delivered to the balloon, which helps compensate for lack of precision by the clinician. The stop mechanism 20 may be mounted on the syringe 60 during production, or as separate components that can be retro-fit onto an existing supply of syringes.

Referring to FIGS. 33, 34A, 34B, and 35, the catheter 62 has the sealing member 930 inserted into its proximal end and has a side-access inflation port 17, shown in greater detail in FIGS. 34A and 34B. The inflation port 17, proximal end of the catheter 62 and distal end of the sealing member 930 are positioned within the inflation adapter 30 (see FIG. 35) to which a syringe assembly 100 in accordance with the present invention has been operably coupled. The inflation syringe 60 is coupled via an injection cap 22 at its distal end to a valve 68 that also connects the large capacity syringe 64 and a short tube segment 216. The tube segment 216 is adapted to connect to a fitting or male luer member 24 of the inflation adapter 30. Thus, the sealing member 930 is engaged by the adapter 30 to allow use of the low volume syringe 60 of the syringe assembly 100 to inflate the balloon 66 at the end of the catheter 62.

The catheter 62 (depicted in FIGS. 34A and 34B) has a proximal end 912, and a distal end (not shown in FIGS. 34A and 34B) to which is mounted the inflatable balloon 66. A central lumen 940 extends within a tubular body 918 between the proximal and distal ends. An opening 923 to lumen 940 is present at the proximal end 912 of catheter 62. The inflation port 17 in fluid communication with lumen 940 is provided on tubular body 918.

The sealing member 930 is inserted into lumen 940 through central lumen opening 923. Sealing member 930 has a first region 935 which has an outer diameter substantially the same as the outer diameter of the proximal end 912 of the catheter tubular body. Region 935 has a taper 934, reducing in diameter to a second region 933 which has an outer diameter less than the inner diameter of lumen 940. In one embodiment, region 933 tapers over length 931 to form a plug mandrel wire 932. As a consequence, region 933 and plug mandrel wire 932 are slidably insertable into the proximal opening 923 of catheter 62 and may move within lumen 940. In one preferred embodiment, region 935 has an outer diameter of about 0.013 inches, region 933 has an outer diameter of about 0.008 inches, and plug mandrel wire 932 has a diameter of about 0.006 inches, with region 933 and plug mandrel wire 932 being inserted into a catheter having a central lumen 940 with an inner diameter of about 0.009 inches.

The length of sealing member region 935 extending proximally of catheter 62 may vary in length depending upon the intended use environment. For example, where catheter 62 is to be used as a guide for other catheters in an "over-the-wire" embodiment, it is preferred that the total length of catheter 62 and sealing member region 935 be about 300 centimeters. Alternately, where catheter 62 is to be used in a single operator or rapid exchange embodiment, it is preferred that the total length of catheter 62 and region 935 be about 190 centimeters. Accordingly, with a known catheter length and use environment, an appropriate length for region 935 may be chosen.

Regions 935 and 933 and plug mandrel wire 932 may all be made out of metals such as stainless steel. Alternatively, combinations of materials may be used as well. For example, in some applications it may be desirable to manufacture regions 935 and 933 out of stainless steel, while manufacturing plug mandrel wire 932 out of nitinol. Furthermore, the various sealing member regions may be made from a single metal wire strand coined at various points to achieve the desired dimensional tolerances, or multiple segments may be joined together to form sealing member 930.

Where multiple segments are joined, region 935, region 933, and plug mandrel wire 932 are attached to one another by any suitable means of bonding metal to metal, such as crimping, soldering, brazing, adhesives and the like. In one preferred embodiment, cyanoacrylate adhesives are used to adhere these various parts of sealing member 930 to one another.

As illustrated in FIGS. 34A and 34B, the outer diameter of sealing member region 933 is less than the inner diameter of lumen 940, such that region 933 is slidably insertable into lumen 940. In addition, the outer diameters of the tapered portions 931 and wire 932 are also small enough such that they too are slidably insertable in lumen 940. However, the outer diameter of region 935 is greater than the inner diameter 940, and thus only a small portion of tapered portion 934 of sealing member 930 between region 935 and region 933 is insertable into lumen 940 through opening 923. Advantageously, this provides for a snug interference fit when sealing member 930 is fully inserted into catheter 62. This interference fit provides a frictional force which counteracts the tendency of the pressurized fluids and internal wire flexing in the catheter to push sealing member 930 out of opening 923.

As illustrated in FIGS. 34A and 34B, sealing member 930 has movement-force increasing structure which increases the force required to move sealing member 930 within lumen 940. The movement-force increasing structure consists of waves 938*a* and 938*b* formed in wire 932 near its distal end. Waves 938*a* and 938*b* contact the inner surface of lumen 940, thereby increasing the frictional force which must be overcome to move wire 932 within lumen 940. In one preferred embodiment, wire 932 is made of nitinol and has an outer diameter of about 0.006 inches, and is inserted into a nitinol catheter which has an inner lumen 940 with a diameter of about 0.009 inches. In one embodiment, waves are formed on wire 932 for 3 cycles with an amplitude of about 0.019 inches to increase the valve-opening movement force. Alternatively, by increasing the length over which wire 932 contacts the inner wall of the tubular body 918, the frictional forces may be increased.

A lumen sealer portion 936 is coaxially and fixedly mounted on wire 932. Sealer portion 936 forms a fluid tight seal with the outer diameter of wire 932 and the inner diameter of lumen 940, such that fluid introduced into lumen 940 through the inflation port 17 is prevented from flowing past sealer portion 936 when sealer portion 936 is inserted into lumen 940 distally of the inflation port 17. Sealer portion 936 forms the fluid tight seal by firmly contacting the entire inner circumference of a section of lumen 940 along a substantial portion of the length of sealer portion 936.

As shown in FIG. 34A, sealer portion 936 is positioned proximally of the inflation port 17, so that an unrestricted fluid passageway exists between inflation port 17 and the inflatable balloon at the distal end of catheter 62, which is like a valve "open" position. In this position, region 933 is shown partially withdrawn from opening 923. Referring to FIG. 34B, sealer portion 936 is positioned distally of inflation port 17, so that fluid flow between inflation port 17 and the inflatable balloon 66 at the distal end of catheter 62 are substantially blocked, which is like a valve "closed" position.

Catheter 62 is changed from the valve open position to the valve closed position by the movement of sealing member 930 and its various components. Preferably, the exact length of movement needed to change catheter 62 from the valve closed to the valve open position is built into the movement function of the adaptor used to manipulate sealing member 930 thereby opening and closing the catheter valve. In this regard, it is preferred that catheter 62 be used with an adaptor such as adaptor 30, which provides for such controlled precise movement.

The "stroke-length", or overall movement in one dimension, of sealing member 930 required to open or close the valve may be varied depending upon the catheter requirements. When relying upon the inflation adaptor to control movement, however, it is important that the movement of the controlling elements of the adaptor be coordinated with those of sealing member 930.

Referring to FIGS. 33 and 35, the inflation adapter 30 comprises a housing having two halves 34, 36 preferably formed of metal, medical grade polycarbonate, or the like. In one embodiment, the halves 34, 36 are attached by hinges 205 to be separated or joined in a clam shell manner. A locking clip 38 secures the halves while the adapter 30 is in use. A groove within the housing has a width to accept the proximal end of the catheter 62 having the sealing member 930. The male luer member 24 (FIG. 33), or other suitable connector, extrudes from a top of the housing to provide an inflation passageway. Seals 70 are provided within the housing and around the internal segment 285 of the inflation pathway to conduct the pressurized fluid provided by the syringe 60 attached to the male luer member 24.

An actuator 40, shown in FIG. 33 at the top of the adapter housing, controls a cam which operates sliding panels 291 (FIG. 35) contained in the housing. Preferably, the catheter 62 is positioned within the housing with the sealing member 930 in the closed position (FIG. 34B), such that the side inflation port 17 is located in the sealed inflation area 285 of the housing. An adjacent proximal portion of the catheter 62 extends outside the housing (and into the patient), and a proximal portion of the sealing member 930 extends out of the other side of the housing. The locking clip 38 is then secured and then the syringe 60 may be attached. The actuator 40 is moved from a first position to a second position, such that the sliding panels 291 within the housing cause the sealing member 930 to be in an open position to allow fluid flow through the inflation port 17 (FIG. 34A). "Closing" the sealing member 930 is accomplished by moving the actuator 40 from the second position back to the first position (FIG. 34B), such that the balloon inflation is maintained.

Further details regarding catheter valves, catheter balloons, and inflation adaptors are found in copending application Ser. No. 09/025,991 entitled "Syringe and Method for Inflating Low Volume Catheter Balloons" filed Feb. 19, 1998, now abandoned, and Ser. No. 08/975,723 entitled "Low Profile Catheter Valve and Inflation Adaptor" filed Nov. 20, 1997, now U.S. Pat. No. 6,050,972, both of which are hereby incorporated by reference herein.

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

What is claimed is:

1. A method for the treatment of an occlusion in a branch of a bifurcated blood vessel having a common portion and two branches, such as the carotid artery, comprising:

providing an elongate member having an occlusive device at a distal end portion thereof;

delivering the elongate member through the common portion of the bifurcated vessel and into a branch of the bifurcated vessel, such as the internal carotid artery;

positioning the occlusive device in said branch distal of the occlusion;

sliding a therapy catheter on the elongate member;

occluding said branch only on the distal side of the occlusion by actuating the occlusive device;

treating the occlusion with the therapy catheter;

providing a second catheter having a fluid flow lumen in fluid communication with a fluid flow opening at a distal end portion of the second catheter;

continuing occlusion of said branch using the occlusive device while:

(a) positioning the fluid flow opening of the second catheter in said branch of the vessel at a location between the occlusive device and the treated occlusion;

(b) applying fluid pressure to the fluid flow lumen to cause fluid flow along said branch, between (i) an intersection of said branch with the common portion and (ii) said location, whereby fluid flows across the treated occlusion; and deactuating the occlusive device.

2. The method of claim 1, comprising removing the therapy catheter from said branch of the vessel prior to applying the fluid pressure.

3. The method of claim 1, wherein the fluid flow across the treated occlusion flushes emboli in said branch away from the treated occlusion.

4. The method of claim 1, wherein said applying fluid pressure comprises aspirating fluid into the lumen to draw emboli away from the treated occlusion and into the lumen.

5. The method of claim 4, wherein fluid is aspirated at a rate between 0.5 and 5 cc/sec.

6. The method of claim 4, wherein fluid is aspirated at a rate of between 0.5 to 1.1 cc/sec.

7. The method of claim 1, wherein said applying fluid pressure comprises irrigating through the second catheter.

8. The method of claim 7, wherein said method further comprises ejecting sufficient irrigation fluid from the second catheter to transport emboli from the treated occlusion along said branch to the intersection, whereby the emboli are flushed down another branch of the bifurcated vessel.

9. The method of claim 8, wherein the irrigation fluid has a flow rate of between 0.1 and 5 cc/sec.

10. The method of claim 8, wherein the irrigation fluid has a flow rate of between 0.5 and 2 cc/sec.

11. The method of claim 1, wherein the second catheter is an intermediate catheter.

12. The method of claim 1, comprising allowing blood to flow from the common portion of the bifurcated vessel through another branch of the vessel during said using of the occlusive device to occlude said branch.

13. The method of claim 1, comprising applying the fluid pressure to the fluid flow lumen in the form of pulses.

14. The method of claim 1, wherein said providing the elongate member comprises providing a distal elongate member portion that is more flexible than a proximal elongate member portion.

15. The method of claim 1, wherein said applying fluid pressure comprises first aspirating and then irrigating.

16. The method of claim 1, comprising:

positioning an outer catheter such that a portion of the outer catheter is in the common portion of the vessel, the outer catheter having a radial extent that permits the therapy catheter and the second catheter to pass through the outer catheter; and irrigating through the second catheter while simultaneously aspirating through the outer catheter.

17. The method of claim 16, wherein a fluid flow opening of the outer catheter is positioned proximal to the treated lesion.

18. The method of claim 1, wherein the blood vessel is the carotid artery.

19. The method of claim 1, wherein said treating the occlusion comprises balloon angioplasty or deploying a stent.

20. The method of claim 1, wherein said actuating the occlusive device comprises inflating an occlusion balloon.

21. The method of claim 20, wherein the balloon is of a compliant material.

22. The method of claim 1, wherein the elongate member is a tubular metallic guidewire.

23. A method for the treatment of an occlusion in a branch of a bifurcated blood vessel having a common portion and two branches, such as the carotid artery, comprising:

providing an elongate member having an occlusive device at a distal end portion thereof;

delivering the elongate member through the common portion of the bifurcated vessel and into a branch of the bifurcated vessel, such as the internal carotid artery;

positioning the occlusive device in said branch distal of the occlusion;

sliding a therapy catheter on the elongate member;

occluding said branch on the distal side of the occlusion by actuating the occlusive device;

treating the occlusion with the therapy catheter;

removing the therapy catheter from said branch of the vessel;

providing a second catheter having a fluid flow lumen in fluid communication with a fluid flow opening at a distal end portion of the second catheter;

sliding the second catheter on the elongate member after said removal of the therapy catheter;

continuing occlusion of said branch using the occlusive device while:
   (a) positioning the fluid flow opening of the second catheter in said branch of the vessel at a location between the occlusive device and the treated occlusion;
   (b) applying fluid pressure to the fluid flow lumen to cause fluid flow along said branch, between (i) an intersection of said branch with the common portion and (ii) said location, whereby fluid flows across the treated occlusion; and deactuating the occlusive device.

24. The method of claim 23, wherein said applying fluid pressure comprises aspirating fluid into the lumen to draw emboli away from the treated occlusion and into the lumen.

25. The method of claim 24, wherein fluid is aspirated at a rate between 0.5 and 5 cc/sec.

26. The method of claim 24, wherein fluid is aspirated at a rate of between 0.5 to 1.1 cc/sec.

27. The method of claim 23, wherein said applying fluid pressure comprises irrigating through the second catheter.

28. The method of claim 27, wherein said method further comprises ejecting sufficient irrigation fluid from the second catheter to transport emboli from the treated occlusion along said branch to the intersection, whereby the emboli are flushed down another branch of the bifurcated vessel.

29. The method of claim 28, wherein the irrigation fluid has a flow rate of between 0.1 and 5 cc/sec.

30. The method of claim 28, wherein the irrigation fluid has a flow rate of between 0.5 and 2 cc/sec.

31. The method of claim 23, comprising applying the fluid pressure to the fluid flow lumen in the form of pulses.

32. The method of claim 23, further comprising inflating a balloon on an outer catheter within the common portion of the vessel to occlude the common portion.

33. The method of claim 23, wherein the elongate member is a tubular metallic guidewire.

34. A method for the treatment of an occlusion in a carotid artery, comprising, in order:

delivering a main catheter into said artery, until a distal end of said catheter is proximal to said occlusion;

delivering an inner catheter having a occlusive device on its distal end into said artery, until said occlusive device is distal to said occlusion;

activating said occlusive device to occlude said artery distal to said occlusion;

delivering a therapy catheter into said artery until it reaches said occlusion;

performing therapy on said occlusion;

removing said therapy catheter from said patient;

delivering a distal end of an intermediate catheter proximal to said occlusive device;

aspirating an area proximal to said occlusive device using said intermediate catheter to remove particles and debris; and irrigating said area proximal to said occlusive device using said intermediate catheter following said aspirating.

35. The method of claim 34, wherein the intermediate catheter comprises a single lumen and said aspirating and said irrigating are performed through said lumen.

36. The method of claim 34, wherein the intermediate catheter comprises two or more lumens, and said aspirating and said irrigating are performed through different lumens.

37. The method of claim 34, wherein said occlusive device is a balloon and said activating comprises inflating said balloon.

38. The method of claim 34, wherein said occlusive device is a filter and said activating comprises deploying said filter to prevent migration of particles downstream.

39. The method of claim 34, wherein said performing therapy comprises performing a method selected from the group consisting of delivering a drug directly to the site of said occlusion, performing balloon angioplasty, deploying a stent, and performing atherectomy.

40. The method of claim 34, wherein said therapy catheter is selected from the group consisting of a thrombectomy catheter, a rheolitic device, and a device which creates a venturi effect within the vessel.

41. The method of claim 34, wherein said main catheter further comprises an occlusive device mounted on its distal end, and wherein said method further comprises activating said occlusive device on said main catheter prior to delivering said inner catheter.

* * * * *